United States Patent [19]

Tsubotani et al.

[11] Patent Number: 5,679,708
[45] Date of Patent: Oct. 21, 1997

[54] EPOXYSUCCINIC ACID DERIVATIVES, THEIR PRODUCTION AND USE

[75] Inventors: Shigetoshi Tsubotani; Masayuki Takizawa, both of Ibaraki; Junji Mizoguchi, Osaka, all of Japan

[73] Assignee: Takeda Chemical Industries, Ltd., Osaka, Japan

[21] Appl. No.: 513,895

[22] PCT Filed: May 25, 1995

[86] PCT No.: PCT/JP95/01004

§ 371 Date: Sep. 5, 1995

§ 102(e) Date: Sep. 5, 1995

[87] PCT Pub. No.: WO95/32954

PCT Pub. Date: Dec. 7, 1994

[30] Foreign Application Priority Data

May 31, 1994 [JP] Japan ................................. 6-119206
Aug. 8, 1994 [JP] Japan ................................. 6-186166

[51] Int. Cl.$^6$ ..................... C07D 303/48; C07D 405/12; A61K 31/335
[52] U.S. Cl. ......................... 514/475; 549/548; 549/549
[58] Field of Search ................... 514/475; 549/548, 549/549

[56] References Cited

U.S. PATENT DOCUMENTS 4,333,879 6/1982 Tamai et al. ......................... 549/549

FOREIGN PATENT DOCUMENTS 7-70098 3/1995 Japan.

OTHER PUBLICATIONS

Kakegawa et al., "Participation of cethepsin L on bone resorption", FEBS, vol. 321, pp. 247–250, 1993.

Primary Examiner—Bernard Dentz
Assistant Examiner—Lyman H. Smith
Attorney, Agent, or Firm—Wenderoth, Lind & Ponack

[57] ABSTRACT

The present invention relates to a compound of the formula:

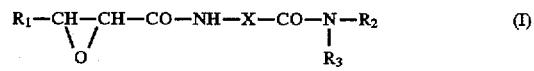

wherein $R_1$ stands for an optionally esterified or amidated carboxyl group, X stands for an optionally substituted divalent hydrocarbon residue, $R_2$ stands for hydrogen or an optionally substituted hydrocarbon residue, $R_3$ stands for an alkyl group which is substituted with a group bonded through O or $S(O)_n$ wherein n is 0, 1 or 2, with a proviso that when the partial structural formula: —NH—X—CO— is leucine residue, $R_3$ is not 3-hydroxy-3-methylbutyl group nor 4-hydroxy-3-methylbutyl group, or a salt thereof, which is useful as prophylactic and therapeutic agents of bone diseases and as inhibitory agents of thiol protease.

23 Claims, No Drawings

EPOXYSUCCINIC ACID DERIVATIVES, THEIR PRODUCTION AND USE

This application is a 35 USC 371 National Stage filing of PCT/JP95/01004 published as WO95/32954 on Dec. 7, 1994.

BACKGROUND OF THE INVENTION

1. Field of the Invention

This invention relates to novel epoxysuccinic acid derivatives, which are useful as prophylactic and therapeutic agents of bone diseases and agents of inhibiting thiol protease.

2. Description of Related Art

In bone tissue, bone resorption and formation occur constantly with a good balance to ensure bone homeostasis; bone diseases such as osteoporosis are caused when the balance shifts to the bone resorption side. In recent years, various epoxy compounds possessing prophylactic and therapeutic activity against bone diseases have been reported (JPA H2(1990)-218610, EPA269311).

And, as an in vivo metabolite of loxistatin, a side chain hydroxide has been reported [K. Fukushima et al., Xenobiotica, Vol. 20, p. 1043 (1990)].

Currently, bone resorption suppressors such as estrogens and calcitonin are used for the prophylaxis and therapy of bone diseases such as osteoporosis. However, in the case of administration of these therapeutic agents, subjects to be administered are limited, and their efficacy is uncertain in some instances, and satisfactory effects have not yet been brought about. And, at the present stage, compounds showing satisfactory inhibiting action against thiol protease have not yet been available.

SUMMARY OF THE INVENTION

With the above situation in mind, the present inventors have directed their attention to thiol protease, especially cathepsin L [H. Kakagawa et al., FEBS Letters, Vol. 321, p. 247 (1993)], which has recently been shown to play a major role in bone resorption. They have conducted a diligent study and found that novel epoxysuccinic acid derivatives show potent actions of inhibiting cathepsin L and, further, of suppressing bone resorption.

Based on these findings, the present inventors have made a further study to accomplish the present invention.

According to the present invention, there is provided:
(1) a compound of the formula:

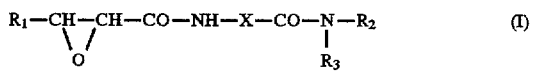

$$R_1-CH-CH-CO-NH-X-CO-N-R_2 \quad (I)$$
(with epoxide O bridging the two CH groups, and $R_3$ on the N)

wherein $R_1$ stands for an optionally esterified or amidated carboxyl group, X stands for an optionally substituted divalent hydrocarbon residue, $R_2$ stands for hydrogen or an optionally substituted hydrocarbon residue, $R_3$ stands for an alkyl group which is substituted with a group bonded through O or $S(O)_n$ wherein n is 0, 1 or 2, with a proviso that when the partial structural formula: —NH—X—CO— is leucine residue, $R_3$ is not 3-hydroxy-3-methylbutyl group nor 4-hydroxy-3-methylbutyl group or a salt thereof, (2) the compound according to term (1) above, wherein $R_1$ is an optionally esterified carboxyl group, (3) the compound according to term (1) above, wherein the partial structural formula: —NH—X—CO— is an α-amino acid residue, (4) the compound according to term (3) above, wherein the α-amino acid residue is an aromatic amino acid residue, (5) the compound according to term (3) above, wherein the α-amino acid is of L-configuration, (6) the compound according to term (1) above, wherein X is a divalent hydrocarbon residue having a cyclic group, (7) the compound according to term (1) above, wherein $R_2$ is hydrogen, (8) the compound according to term (1) above, wherein $R_2$ is $C_{1-16}$ hydrocarbon residue, (9) the compound according to term (1) above, wherein the alkyl group is $C_{1-15}$ alkyl group,

(10) the compound according to term (1) above, wherein $R_3$ is an alkyl group which is substituted with a group bonded through O,

(11) the compound according to term (10) above, wherein the group bonded through O is $C_{1-16}$ hydrocarbon-oxy group,

(12) the compound according to term (11) above, wherein the $C_{1-16}$ hydrocarbon-oxy group is $C_{1-6}$ alkoxy group,

(13) the compound according to term (1) above, wherein $R_3$ is an alkyl group which is substituted with a group bonded through $S(O)_n$ wherein n is 0, 1 or 2,

(14) the compound according to term (13) above, wherein the group bonded through $S(O)_n$ is $C_{1-14}$ hydrocarbon-S$(O)_n$ group,

(15) the compound according to term (14) above, wherein the $C_{1-14}$ hydrocarbon-S$(O)_n$ group is $C_{1-6}$ alkylthio group,

(16) the compound according to term (1) above, wherein the compound is N-[N-[(2S,3S)-3-trans-ethoxycarbonyloxirane-2-carbonyl]-L-phenylalanyl]-1-amino-3-methoxypropane,

(17) the compound according to term (1) above, wherein the compound is N-[N-[(2S,3S)-3-trans-ethoxycarbonyloxirane-2-carbonyl]-L-phenylalanyl]-1-amino-3-methylthiopropane,

(18) a composition for inhibition of thiol protease, which comprises a compound or a salt thereof as defined in term (1) above,

(19) a pharmaceutical composition which comprises a compound or a salt thereof as defined in term (1) above,

(20) a pharmaceutical composition for preventing or treating a bone disease, which comprises a compound or a salt thereof as defined in term (1) above,

(21) the pharmaceutical composition according to term (20) above, wherein the bone disease is osteoporosis,

(22) use of a compound or a salt thereof according to term (1) above, for the manufacture of a medicament for inhibition of a thiol protease,

(23) use of a compound or a salt thereof according to term (1) above, for the manufacture of a medicament for preventing or treating a bone disease,

(24) the use according to term (23) above, wherein the bone disease is osteoporosis,

(25) a method for inhibiting a thiol protease in a mammal, which comprises administering an effective amount of the compound as defined in term (1) above or a pharmaceutically acceptable salt thereof to the mammal,

(26) a method for preventing or treating a bone disease in a mammal, which comprises administering an effective amount of the compound as defined in term (1) above or a pharmaceutically acceptable salt thereof to the mammal, and

(27) the method according to term (26) above, wherein the bone disease is osteoporosis.

DETAILED DESCRIPTION OF THE INVENTION

Abbreviations for amino acids and peptides used in the present specification are based on abbreviations specified by the IUPAC-IUB Commission on Biochemical Nomenclature or abbreviations in common use in relevant fields. When the amino acid may exist as acid, it is of the L-configuration, unless otherwise stated.

With respect to general formula (I), the carboxyl group for $R_1$ which may optionally be esterified is exemplified by pharmaceutically acceptable ones or those convertible to pharmaceutically acceptable ones in vivo. Preferable esterified carboxyl groups are represented by the formula, —COOR$_4$ [wherein R$_4$ stands for, for example, (1) $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.) optionally having 1 to 3 substituents selected from (a) nitro group, (b) halogen (e.g. bromine, chlorine, fluorine, etc.) and (c) $C_{2-6}$ alkanoyloxy groups (e.g. acetyloxy, propionyloxy, isopropionyloxy, butyryloxy, isobutyryloxy, valeryloxy, isovaleryloxy, pivaloyloxy, hexanoyloxy, etc.), (2) $C_{6-14}$ aryl groups (e.g. phenyl, naphthyl, etc.) optionally having 1 to 3 substituents selected from (a) nitro group, (b) halogen (e.g. bromine, chlorine, fluorine, etc.) and (c) $C_{1-4}$ alkoxy groups (e.g. methoxy, ethoxy, propoxy, isopropoxy, butoxy, isobutoxy, sec-butoxy, tert-butoxy, etc.) and (3) $C_{7-12}$ aralkyl groups (e.g. benzyl, phenethyl, etc.) optionally having 1 to 3 substituents selected from (a) nitro group, (b) halogen (e.g. bromine, chlorine, fluorine, etc.) and (c) $C_{1-4}$ alkoxy groups (e.g. methoxy, ethoxy, propoxy, isopropoxy, butoxy, isobutoxy, sec-butoxy, tert-butoxy, etc.).

Preferable examples of R$_4$ include $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.) optionally having 1 to 3 substituents selected from (a) nitro group, (b) halogen (e.g. bromine, chlorine, fluorine, etc.) and (c) $C_{2-6}$ alkanoyloxy groups (e.g. acetyloxy, propionyloxy, isopropionyloxy, butyryloxy, isobutyryloxy, valeryloxy, isovaleryloxy, pivaloyloxy, hexanoyloxy, etc.).

More preferable examples of R$_4$ include $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.).

With respect to general formula (I), the carboxyl group for $R_1$ which may optionally be amidated is exemplified by pharmaceutically acceptable ones or those which are convertible into pharmaceutically acceptable ones in vivo. Preferable amidated carboxyl groups are represented by the formula, —CONHR$_5$, wherein R$_5$ stands for, for example, (1) hydrogen, (2) $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.) optionally having 1 to 3 substituents selected from (a) nitro group and (b) halogen (e.g. bromine, chlorine, fluorine, etc.), (3) $C_{6-14}$ aryl groups (e.g. phenyl, naphthyl, etc.) optionally having 1 to 3 substituents selected from (a) nitro group, (b) halogen (e.g. bromine, chlorine, fluorine, etc.) and (c) $C_{1-4}$ alkoxy groups (e.g. methoxy, ethoxy, propoxy, isopropoxy, butoxy, isobutoxy, sec-butoxy, tert-butoxy, etc.), and (4) $C_{7-12}$ aralkyl groups (e.g. benzyl, phenethyl, etc.) optionally having 1 to 3 substituents selected from (a) nitro group, (b) halogen (e.g. bromine, chlorine, fluorine, etc.) and (c) $C_{1-4}$ alkoxy groups (e.g. methoxy, ethoxy, propoxy, isopropoxy, butoxy, isobutoxy, sec-butoxy, tert-butoxy, etc.).

Preferable examples of R$_5$ include $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.) optionally having 1 substituents selected from (a) nitro group and (b) halogen (e.g. bromine, chlorine, fluorine, etc.).

More preferable examples of R$_5$ include $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.).

With respect to general formula (I), R$_1$ is preferably an optionally esterified carboxyl group. More preferably, R$_1$ is a carboxyl group optionally esterified by $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.).

With respect to general formula (I), preferable examples of the divalent hydrocarbon residue in optionally substituted divalent hydrocarbon residues for X include $C_{1-20}$ divalent aliphatic hydrocarbon residues.

Examples of the divalent aliphatic hydrocarbon residue include straight-chain or branched saturated hydrocarbon residues represented by —$C_mH_{2m}$— ($1 \leq m \leq 15$, m is an integer) (e.g. methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, methylmethylene, ethylmethylene, propylmethylene, isopropylmethylene, butylmethylene, isobutylmethylene, sec-butylmethylene, tert-butylmethylene, ethylethylene, propylene, etc.), straight-chain or branched unsaturated hydrocarbon residues represented by —$C_pH_{2(p-q)}$— ($2 \leq p \leq 15$, p>q, p and q are an integer) (e.g. propenylene, vinylene, etc.) and aliphatic cyclic hydrocarbon residues represented by —$C_rH_{2(r-1)}$— ($3 \leq r \leq 15$, r is an integer) (e.g. cyclohexylene and cyclopentylene). Preferable divalent aliphatic hydrocarbon residues are straight-chain or branched saturated hydrocarbon residues represented by —$C_mH_{2m}$— ($1 \leq m \leq 15$, m is an integer).

With respect to general formula (I), examples of the substituents in optionally substituted divalent hydrocarbon residues for X include (1) amino group, (2) mono- or di-$C_{1-4}$ alkylamino groups (e.g. methylamino, ethylamino, propylamino, isopropylamino, n-butylamino, dimethylamino, diethylamino, etc.), (3) $C_{1-6}$ alkanoylamino groups (e.g. formylamino, acetylamino, propionylamino, isopropionylamino, butyrylamino, isobutyrylamino, valerylamino, isovalerylamino, pivaloylamino, hexanoylamino, etc.), (4) $C_{7-11}$ arylcarbonylamino groups (e.g. benzoylamino, p-toluoylamino, 1-naphthoylamino, 2-naphthoylamino, etc.), (5) $C_{2-5}$ alkoxycarbonylamino groups (e.g. methoxycarbonylamino, ethoxycarbonylamino, propoxycarbonylamino, isopropoxycarbonylamino, tert-butoxycarbonylamino, etc.), (6) $C_{8-13}$ aralkyloxycarbonylamino groups (e.g. benzyloxycarbonylamino, phenethyloxycarbonylamino, etc.), (7) $C_{1-6}$ alkylsulfonylamino groups (e.g. methylsulfonylamino, ethylsulfonylamino, propylsulfonylamino, etc.), (8) $C_{6-12}$ arylsulfonylamino groups (e.g. phenylsulfonylamino, tosylamino, etc.), (9) hydroxyl group,

(10) $C_{1-4}$ alkoxy groups (e.g. methoxy, ethoxy, propoxy, isopropoxy, butoxy, isobutoxy, sec-butoxy, tert-butoxy, etc.),

(11) $C_{6-10}$ aryloxy groups (e.g. phenoxy, etc.),

(12) $C_{7-12}$ aralkyloxy groups (e.g. benzyloxy, phenethyloxy, etc.),

(13) $C_{1-6}$ alkanoyloxy groups (e.g. formyloxy, acetyloxy, propionyloxy, isopropionyloxy, butyryloxy, isobutyryloxy, valeryloxy, isovaleryloxy, pivaloyloxy, hexanoyloxy, etc.),

(14) $C_{7-11}$ arylcarbonyloxy groups (e.g. benzoyloxy, p-toluoyloxy, 1-naphthoyloxy, 2-naphthoyloxy, etc.),

(15) mercapto group,

(16) $C_{1-4}$ alkylthio groups (e.g. methylthio, ethylthio, propylthio, isopropylthio, butylthio, tert-butylthio, etc.),

(17) $C_{6-10}$ arylthio groups (e.g. phenylthio, naphthylthio, etc.),

(18) sulfino groups,

(19) $C_{1-6}$ alkylsulfinyl groups (methylsulfinyl, ethylsulfinyl, propylsulfinyl, etc.),

(20) $C_{6-10}$ arylsulfinyl groups (e.g. phenylsulfinyl, etc.),

(21) sulfo group,

(22) $C_{1-6}$ alkylsulfonyl groups (e.g. methylsulfonyl, ethylsulfonyl, propylsulfonyl, etc.),

(23) $C_{6-10}$ arylsulfonyl groups (phenylsulfonyl, tosyl, etc.),

(24) carboxyl group,

(25) $C_{2-5}$ alkoxycarbonyl groups (e.g. methoxycarbonyl, ethoxycarbonyl, propoxycarbonyl, butoxycarbonyl, tert-butyoxycarbonyl, etc.),

(26) $C_{8-13}$ aralkyloxycarbonyl groups (e.g. benzyloxycarbonyl, phenethyloxycarbonyl, etc.),

(27) $C_{7-11}$ aryloxycarbonyl groups (e.g. phenoxycarbonyl, etc.),

(28) carbamoyl group,

(29) mono- or di- $C_{1-4}$ alkylcarbamoyl groups (e.g. methylcarbamoyl, ethylcarbamoyl, propylcarbamoyl, isopropylcarbamoyl, butylcarbamoyl, dimethylcarbamoyl, diethylcarbamoyl, etc.),

(30) 5- or 6-membered heterocyclic groups or their condensed heterocyclic groups containing, besides carbon atoms, 1 to 4 hetero-atoms selected from oxygen, sulfur, nitrogen etc. (e.g. 2- or 3-thienyl, 2- or 3-furyl, 2- or 3-pyrrolyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl, indolyl, etc.), optionally having 1 to 4 substituents selected from (a) halogen atoms (e.g. fluorine, chlorine, bromine, iodine, etc.), (b) $C_{1-4}$ alkyl groups (e.g. methyl, ethyl, propyl, isopropyl, etc.), (c) halogenophenoxy etc. (e.g. o-, m- or p-chlorophenoxy, o-, m- or p-bromophenoxy, etc.) and (d) hydroxyl group, etc.,

(31) nitro group, (32) cyano group, (33) halogen atoms (e.g. fluorine, chlorine, bromine, iodine, etc.), (34) guanidyl groups optionally substituted with nitro group, (35) amidino group, (36) $C_{6-14}$ aryl groups (e.g. phenyl, naphthyl, etc.) optionally having 1 to 3 substituents selected from (a) halogen atoms (e.g. fluorine, chlorine, bromine, iodine, etc.), (b) nitro group, (c) hydroxyl group and (d) $C_{1-4}$ alkoxy groups (e.g. methoxy, ethoxy, propoxy, isopropoxy, butoxy, isobutoxy, sec-butoxy, tert-butoxy, etc.), and (37) $C_{3-8}$ cycloalkyl groups (e.g. cyclopropyl, cyclobutyl, cyclopentyl, cyclohexyl, etc.) optionally having 1 to 3 substituents selected from (a) halogen atoms (e.g. fluorine, chlorine, bromine, iodine, etc.), (b) nitro group, (c) hydroxyl group and (d) $C_{1-4}$ alkoxy groups (e.g. methoxy, ethoxy, propoxy, isopropoxy, butoxy, isobutoxy, sec-butoxy, tert-butoxy, etc.).

Number of substituents range preferably from 1 to 5, more preferably from 1 to 3.

Preferable examples of the above-mentioned substituents are cyclic groups including (1) 5- or 6-membered heterocyclic groups or their condensed heterocyclic groups containing, besides carbon atoms, 1 to 4 hetero-atoms selected from oxygen, sulfur, nitrogen, etc. (e.g. 2- or 3-thienyl, 2- or 3-furyl, 2- or 3-pyrrolyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl, indolyl, etc.) optionally having 1 to 4 substituents selected from (a) halogen atoms (fluorine, chlorine, bromine, iodine, etc.), (b) $C_{1-4}$ alkyl groups (e.g. methyl, ethyl, propyl, isopropyl, etc.), (c) halogenophenoxy (e.g. o-, m- or p-chlorophenoxy, o-, m- or p-bromophenoxy, etc.) and (d) hydroxyl group, (2) $C_{6-14}$ aryl groups (e.g. phenyl, naphthyl, etc.) optionally having 1 to 3 substituents selected from (a) halogen atoms (e.g. fluorine, chlorine, bromine, iodine, etc.), (b) nitro group, (c) hydroxyl group and (d) $C_{1-4}$ alkoxy groups (e.g. methoxy, ethoxy, propoxy, isopropoxy, butoxy, isobutoxy, sec-butoxy, tert-butoxy, etc.), and (3) $C_{3-8}$ cycloalkyl groups (e.g. cyclopropyl, cyclobutyl, cyclopentyl, cyclohexyl, etc.) optionally having 1 to 3 substituents selected from (a) halogen atoms (e.g. fluorine, chlorine, bromine, iodine, etc.), (b) nitro group, (c) hydroxyl group and (d) $C_{1-4}$ alkoxy groups (e.g. methoxy, ethoxy, propoxy, isopropoxy, butoxy, isobutoxy, sec-butoxy, tert-butoxy, etc.).

With respect to general formula (I), X stands for, preferably, divalent hydrocarbon residues having the above-mentioned cyclic groups.

With respect to general formula (I), the partial structural formula: —NH—X—CO— is preferably an amino acid residue. The amino acid is exemplified by an amino acid which constitutes protein or an amino acid obtainable from natural sources as metabolites of microorganisms or components of animals and vegetables.

Examples of amino acids which constitute protein include aliphatic monoaminocarboxylic acids (e.g. glycine, alanine, valine, leucine, isoleucine, etc.), aliphatic hydroxylamino acids (e.g. serine, threonine, etc.), acidic amino acids (e.g. aspartic acid, glutamic acid, etc.), acidic amino acid amides (e.g. asparagine, glutamine, etc.), aromatic amino acids (e.g. phenylalanine, tyrosine, tryptophane, etc.), basic amino acids (e.g. arginine, lysine, histidine, etc.), sulfur-containing amino acids (e.g. methionine, cystine, cysteine, etc.), etc.

Examples of amino acids obtained as metabolites of microorganisms or components of animals or vegetables, include, among others, aliphatic monoaminocarboxylic acids (e.g. L-α-aminobutyric acid, γ-aminobutyric acid, β-aminoisobutyric acid, β-alanine, homoserine, α-methyl-D-serine, O-carbamyl-D-serine, δ-hydroxy-γ-oxo-norvaline, etc.), monoaminodicarboxylic acids (e.g. L-α-aminoadipic acid, L-theanine, L-γ-methylene glutamic acid, L-γ-methyl glutamic acid, etc.), diaminomonocarboxylic acids (e.g. L-ornithine, β-lysine, α,β-diaminopropionic acid, L-α, γ-diaminobutyric acid, etc.), diaminodicarboxylic acids (e.g. diaminopimelic acid, etc.), sulfur-containing amino acids (e.g. cysteinic acid, etc.), aromatic amino acids, (e.g. kynurenine, 3,4-dihydroxyphenyl-L-alanine, etc.), heterocyclic amino acids, (e.g. 2,3-dicarboxyaziridine, [S]-2-amino-3-(isoxazolin-5-on-4-yl) propionic acid, anticapsin, etc.), basic amino acids (e.g. L-4-oxalysine, oxolysine, [3R,5R]-3,6-diamino-5-hydroxyhexanoic acid, etc.), sulfur-containing amino acids (e.g. lanthionine, S-methyl-L- cysteine, etc.), cyclic amino acids, (e.g. pipecolic acid, azetidine-2-carboxylic acid, [1R,2S]-2-aminocyclopentane-1-carboxylic acid, etc.), amino acids substituted with specific functional groups (e.g. citrulline, alanosine, L-azaserine, etc.).

Preferable examples of amino acid residues represented by the partial structural formula, —NH—X—CO—, are α-amino acid residues. Preferable examples of the α-amino acid residue include residues of aliphatic monoaminocarboxylic acid (e.g. glycine, alanine, valine, leucine, isoleucine, etc.), acidic amino acid (e.g. aspartic acid, glutamic acid, etc.), aromatic amino acid (e.g. phenylalanine, tyrosine, tryptophane, etc.) and basic amino acid (e.g. arginine, lysine, histidine, etc.). The α-amino acid is preferably of L-configuration. More preferable examples of amino acid residues represented by the partial structural formula, —NH—X—CO—, are residues of aromatic amino acids (e.g. phenylalanine, tyrosine, tryptophane, etc.).

With respect to general formula (I), preferable examples of hydrocarbon residues in the optionally substituted hydrocarbon residues for $R_2$ are $C_{1-16}$ hydrocarbon residues, as exemplified by (1) $C_{1-15}$ alkyl groups (e.g. methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, etc.), (2) $C_{3-8}$ cycloalkyl groups (e.g. cyclopropyl, cyclobutyl, cyclopentyl, cyclohexyl, etc.), (3) $C_{2-10}$ alkenyl groups (e.g. vinyl, allyl, 2-methylallyl, 2-butenyl, 3-butenyl, 3-octenyl, etc.), (4) $C_{2-10}$ alkynyl groups (e.g. ethynyl, 2-propynyl, 3-hexynyl, etc.), (5) $C_{3-10}$ cycloalkenyl groups (e.g. cyclopropenyl, cyclopentenyl, cyclohexenyl, etc.), (6) $C_{6-14}$ aryl groups (e.g. phenyl, naphthyl, etc.) and (7) $C_{7-16}$ aralkyl groups (e.g. benzyl, phenethyl, etc.). Among these, $C_{1-15}$ alkyl groups (e.g. methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, etc.) are preferable.

Such hydrocarbon residues may have, at any possible positions, 1 to 5 substituents selected from (1) hydroxyl group, (2) $C_{1-4}$ alkoxy groups (e.g. methoxy, ethoxy, propoxy, isopropoxy, butoxy, isobutoxy, sec-butoxy, tert-butoxy, etc.), (3) $C_{6-10}$ aryloxy groups (e.g. phenoxy, etc.), (4) $C_{7-12}$ aralkyloxy groups (e.g. benzyloxy, phenethyloxy, etc.), (5) $C_{1-6}$ alkanoyloxy groups (e.g. formyloxy, acetyloxy, propionyloxy, isopropionyloxy, butyryloxy, isobutyryloxy, valeryloxy, isovaleryloxy, pivaloyloxy, hexanoyloxy, etc.), (6) arylcarbonyloxy groups (e.g. benzoyloxy, p-toluoyloxy, 1-naphthoyloxy, 2-naphthoyloxy, etc.), (7) mercapto group, (8) $C_{1-4}$ alkylthio groups (e.g. methylthio, ethylthio, propylthio, isopropylthio, butylthio, tert-butylthio, etc.), (9) $C_{6-10}$ arylthio groups (e.g. phenylthio, naphthylthio, etc.), (10) sulfino group, (11) $C_{1-6}$ alkylsulfinyl groups (e.g. methylsulfinyl, ethylsulfinyl, propylsulfinyl, etc.) optionally having 1 to 3 substituents selected from (a) halogen atoms (e.g. chlorine, bromine, fluorine, etc.) and (b) nitro group, (12) $C_{6-10}$ arylsulfinyl groups (e.g. phenylsulfinyl, etc.) optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group, (13) sulfo group, (14) $C_{1-6}$ alkylsulfonyl groups (e.g. methylsulfonyl, ethylsulfonyl, propylsulfonyl, etc.) optionally having 1 to 3 substituents selected from (a) halogen atoms (e.g. chlorine, bromine, fluorine, etc.) and (b) nitro group, (15) $C_{6-10}$ arylsulfonyl groups (e.g. phenylsulfonyl, etc.) optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group, (16) carboxyl group, (17) $C_{2-5}$ alkoxycarbonyl groups (e.g. methoxycarbonyl, ethoxycarbonyl, propoxycarbonyl, butoxycarbonyl, tert-butoxycarbonyl, etc.), (18) $C_{8-13}$ aralkyloxycarbonyl groups (e.g. benzyloxycarbonyl, phenethyloxycarbonyl, etc.), (19) $C_{7-11}$ aryloxycarbonyl groups (e.g. phenoxycarbonyl, etc.), (20) carbamoyl group, (21) mono- or di- $C_{1-4}$ alkylcarbamoyl groups (e.g. methylcarbomoyl, ethylcarbamoyl, propylcarbamoyl, isopropylcarbamoyl, butylcarbamoyl, dimethylcarbamoyl, diethylcarbamoyl, etc.), (22) phosphono group, (23) mono-or di-$C_{1-4}$ alkylphosphono groups (e.g. methylphosphono, ethylphosphono, propylphosphono, isopropylphosphono, butylphosphono, dimethylphosphono, diethylphosphono, etc.), (24) guanidyl group optionally substituted with nitro group, (25) amidino group, (26) nitro group, (27) oxo group, (28) thioxo group, (29) cyano group, (30) halogen (e.g. fluorine, chlorine, bromine, iodine, etc.), (31) 5- or 6-membered heterocyclic groups containing 1 to 4 hetero-atoms selected from oxygen, sulfur, nitrogen, etc., in addition to carbon atoms, or condensed heterocyclic groups thereof (e.g. 2- or 3-thienyl, 2- or 3-furyl, 3- , 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4,-triazolyl, 1H or 2H-tetrazolyl, 2-, 3- or 4-pyridyl, 2-, 4- or 5-pyrimidyl, 3- or 4-pyridazinyl, quinolyl, isoquinolyl, indolyl, etc.), which may optionally have 1 to 4 substituents selected from (a) halogen (e.g. bromine, chlorine, fluorine, etc.), (b) $C_{1-4}$ alkyl groups (e.g. methyl, ethyl, propyl, isopropyl, etc.) and (c) halogenophenoxy (e.g. o-, m- or p-chlorophenoxy, o-, m- or p-bromophenoxy, etc.), and, in the case where the hydrocarbon residue is cycloalkyl, cycloalkenyl, aryl or aralkyl group, the hydrocarbon residue may optionally have 1 to 4 $C_{1-4}$ alkyl groups (e.g. methyl, ethyl, propyl, isopropyl, butyl, etc.) as substituents.

With respect to general formula (I), $R_2$ is preferable hydrogen.

With respect to general formula (I), alkyl groups in the alkyl groups which are substituted with groups bonded through O or S(O)n wherein n is 0, 1 or 2, shown by $R_3$ are exemplified by $C_{1-15}$ alkyl groups (e.g. methyl, ethyl, propyl, isopropyl, butyl,. isobutyl, sec-butyl, tert-butyl, pentyl, isopentyl, neopentyl, hexyl, heptyl octyl, nonyl decyl, undecyl, dodecyl, tridecyl, tetradecyl, pentadecyl, etc.). Preferable examples of the alkyl groups include $C_{1-6}$ alkyl groups (e.g. methyl, ethyl, propyl, isopropyl, butyl, isobutyl, sec-butyl, tert-butyl, pentyl, isopentyl, neopentyl, hexyl etc.).

Such alkyl groups have, at any possible positions, groups bonded through O or S(O)$_n$ wherein n is 0, 1 or 2.

Examples of groups bonded through O include
(1) hydroxyl group,
(2) $C_{1-6}$ alkoxy groups (e.g. methoxy, ethoxy, propoxy, isopropoxy, butoxy, isobutoxy, sec-butoxy, tert-butoxy, etc.) optionally having 1 to 3 substituents selected from
   (a) halogen atoms (e.g. chlorine, bromine, fluorine, etc.) and (b) nitro group,
(3) $C_{6-10}$ aryloxy groups (e.g. phenoxy, etc.) optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group,
(4) $C_{7-12}$ aralkyloxy groups (e.g. benzyloxy, phenethyloxy, etc.) optionally having 1 to 3 substituents selected from
   (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group, (5) $C_{1-6}$ alkanoyloxy groups (e.g. formyloxy, acetyloxy, propionyloxy, isopropionyloxy, butyryloxy, isobutyryloxy, valeryloxy, isovaleryloxy, pivaloyloxy, hexanoyloxy, etc.) optionally having 1 to 3 substituents selected from (a) halogen atoms (e.g. chlorine, bromine, fluorine, etc.) and (b) nitro group, and (6) $C_{7-11}$ arylcarbonyloxy groups (e.g. benzoyloxy, 1-naphthoyloxy, 2-naphthoyloxy, etc.) optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group.

The groups bonded through O are preferably $C_{1-16}$ hydrocarbon-oxy groups. The $C_{1-16}$ hydrocarbon-oxy groups are more preferably $C_{1-6}$ alkoxy groups.

Examples of groups bonded through $S(O)_n$ wherein n is 0, 1 or 2 include (1) mercapto group,
(2) $C_{1-6}$ alkylthio groups (e.g. methylthio, ethylthio, propylthio, etc.) optionally having 1 to 3 substituents selected from (a) halogen atoms (e.g. chlorine, bromine, fluorine, etc.) and (b) nitro group,
(3) $C_{6-10}$ arylthio groups (e.g. phenylthio, etc.) optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group,
(4) sulfeno group,
(5) sulfino group,
(6) $C_{1-6}$ alkylsulfinyl groups (e.g. methylsulfinyl, ethylsulfinyl, propylsulfinyl, etc.) optionally having 1 to 3 substituents selected from (a) halogen atoms (e.g. chlorine, bromine, fluorine, etc.) and (b) nitro group,
(7) $C_{6-10}$ arylsulfinyl groups (e.g. phenylsulfinyl, etc.) optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group,
(8) sulfo group,
(9) $C_{1-6}$ alkylsufonyl groups (e.g. methylsulfonyl, ethylsulfonyl, propylsulfonyl, etc.) optionally having 1 to 3 substituents selected from (a) halogen atoms (e.g. chlorine, bromine, fluorine, etc.) and (b) nitro group, and
(10) $C_{6-10}$ arylsulfonyl groups (e.g. phenylsulfonyl, etc.) optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group.

The groups bonded through $S(O)_n$ are preferably $C_{1-14}$ hydrocarbon-$S(O)_n$ groups. The $C_{1-14}$ hydrocarbon-$S(O)_n$ groups are more preferably $C_{1-6}$ alkylthio groups.

In the general formula (I), $R_3$ is preferably an alkyl group which is substituted with groups bonded through O. More preferable examples of $R_3$ include (1) $C_{1-6}$ alkoxy groups (e.g. methoxy, ethoxy, propoxy, isopropoxy, butoxy, isobutoxy, sec-butoxy, tert-butoxy, etc.) optionally having 1 to 3 substituents selected from (a) halogen atoms (e.g. chlorine, bromine, fluorine, etc.) and (b) nitro group, or (2) alkanoyloxy groups (e.g. formyloxy, acetyloxy, propionyloxy, isopropionyloxy, butyryloxy, isobutyryloxy, valeryloxy, isovaleryloxy, pivaloyloxy, hexanoyloxy, etc.) optionally having 1 to 3 substituents selected from (a) halogen atoms (e.g. chlorine, bromine, fluorine, etc.) and (b) nitro group.

The preferred examples of compound [I] include N-[N-[(2S,3S)-3-trans-ethoxycarbonyloxirane-2-carbonyl]-L-phenylalanyl]-1-amino-3-methoxypropane and N-[N-[(2S,3S)-3-trans-ethoxycarbonyloxirane-2-carbonyl]-L-phenylalanyl]-1-amino-3-methylthiopropane.

A method of producing the above-mentioned compound (I) or a salt thereof is described hereinafter.

Incidentally, protecting groups and reagents often referred to in following text are abbreviated as follows:

Fmoc: 9-fluorenylmethyloxycarbonyl
Z : benzyloxycarbonyl
Boc : tert-butoxycarbonyl
Bzl : benzyl
TFA : trifluoroacetic acid
DCC : N,N'-dicyclohexylcarbodiimide
BOP : benzotriazol-1-yloxytris(dimethylamino)-phosphonium hexafluorophosphate
DIC : N,N'-diisopropylcarbodiimide
HONB: N-hydroxy-5-norbornene-2,3-dicarboxyimide
HOBT: 1-hydroxybenzotriazole
WSC : water-soluble carbodiimide[1-ethyl-3-(3-dimethylaminopropyl)carbodiimide hydrochloride]
R—: R-configuration
S—: S-configuration A compound represented by the above-mentioned general formula (I) or a salt thereof can be produced by reacting a compound represented by the general formula:

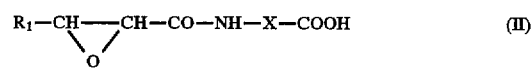

wherein symbols are of the same meaning as defined above, or a salt thereof with a compound represented by the general formula:

wherein symbols are of the same meaning as defined above, or a salt thereof, followed by, when necessary, a deprotection reaction, or by reacting a compound represented by the general formula:

wherein symbols are of the same meaning as defined above, or a salt thereof with a compound represented by the general formula:

wherein symbols are of the same meaning as defined above, or a salt thereof, followed by, when necessary, a deprotection reaction.

The above-mentioned production method employs a conventional means of peptide synthesis, such as liquid phase synthesis or solid phase synthesis. Any optionally chosen known method can be used for such peptide synthesis. For example, the desired compound is produced by the methods described by M. Bondasky and M. Ondetti in "Peptide Synthesis", Interscience, New York (1966); by F. M. Finn and K. Hofmann in "The Proteins, Vol. 2", edited by H. Nenrath and R. L. Hill, Academic Press Inc., New York, (1976); by Nobuo Izumiya et al. in "Peptide Gosei No Kiso To Jikken" Maruzen Co., Ltd. (1985); by H. Yajima, S. Sakakibara et al. in "Seikagaku Jikken Koza 1", edited by the Japanese Biochemical Society, Tokyo Kagaku Dojin (1977); by T. Kimura et al. in "Zoku Seikagaku Jikken Koza 2", edited by the Japanese Biochemical Society, Tokyo Kagaku Dojin (1987); and by J. M. Stewart and J. D. Young in "Solid Phase Peptide Synthesis", Pierce Chemical Company, Illinois (1984), or modifications thereof. Specifically, there may be mentioned the azide method, the chloride method, the acid anhydride method, the mixed acid anhydride method, the DCC method, the active ester method, the method using Woodward reagent K, the carbonylimidazole method, the oxidation-reduction method, the DCC/HONB method, the DIC/HONB method, the DCC/HOBT method, the WSC/HOBT method and the method using BOP reagent, in which compound (II) or a salt thereof or compound (IV) or a salt thereof has its carboxylic acid moiety activated and is then condensed with compound (III) or a salt thereof or compound (V) or a salt thereof, respectively.

With respect to the protection of functional groups, which are not to be involved in the reaction, of the starting materials, the relevant protecting groups, elimination of the protecting groups, activation of the functional groups involved in the reaction, etc., per se known ones or per se known means can be chosen as appropriate.

This reaction may be carried out in the presence of a base. Examples of the base include tertiary amines such as trimethylamine, triethylamine, tripropylamine, N-methylpiperidine, N-methylpyrrolidine, cyclohexyldimethylamine and N-methylmorpholine; secondary amines such as di-n-butylamine, diisobutylamine and dicyclohexylamine; aromatic amine such as pyridine, lutidine and collidine; hydroxides or salts of alkali metals such as lithium, sodium and potassium; and hydroxides or salts of alkaline earth metals such as calcium and magnesium.

In this method, a reactive derivative of carboxylic acid of compound (II) or (IV) is normally used in an amount of 1 mol relative to 1 mol of compound (III) or (V), but it may be used in an excess amount, so long as the reaction is not interfered therewith. When a base is employed, its amount ranges normally from 1 to 5 mol, preferably from 1 to 3 mol relative to 1 mol of compound (III) or (V), while it varies with the starting compound employed, kind of the reactive derivative of carboxylic acid and other reaction conditions.

This reaction is normally carried out in a solvent which does not exert undesirable influence on the reaction. The solvent is selected from those known as useful in peptide condensation reaction. Examples of the solvent include amides such as formamide, N,N-dimethylforamide and N-methylpyrrolidone; sulfoxides such as dimethyl sulfoxide; aromatic amines such as pyridine; halogenated hydrocarbons such as chloroform and dichloromethane; ethers such as tetrahydrofuran and dioxane; nitriles such as acetonitrile; esters such as ethyl acetate and ethyl formate; or appropriate mixtures thereof.

While reaction temperatures are not limitative so long as the reaction proceeds, they are usually within the range from −50° C. to 150° C., preferably from −30° C. to 80° C. Reaction time ranges usually from several ten minutes to several ten hours, while varying with starting materials, bases, reaction temperatures and kinds of solvent then employed.

A compound represented by general formula (I) or a salt thereof can be produced by subjecting a compound or salt thereof produced by the above-described method to a deprotection reaction, when necessary. The deprotection reaction can be carried out by a per se known method such as a method commonly employed in peptide chemistry (cf.: Gosei Kagaku Series, Peptide Gosei, by N. Izumiya, M. Ohno, T. Kato and T. Aoyagi, published by Maruzen Co., Ltd., 1975).

The deprotection reaction for the amino group protected by a urethane type protecting group is carried out in contact with an acid in the absence of a solvent or in a solvent which does not interfere with the reaction. The solvent is exemplified by halogenated hydrocarbons (e.g. dichloromethane, chloroform, 1,2-dichloroethane, etc.), alcohols (e.g. methanol, ehtanol, etc.), water and appropriate mixtures thereof. The acid is exemplified by haloacetic acids (e.g. trifluoroacetic acid, etc.), hydrohalogenic acids (e.g. hydrochloric acid, hydrobromic acid, etc.), etc.

It is advantageous that the N-benzyloxycarbonyl (Z) group and the N-4-methoxybenzyloxycarbonyl group is eliminated by catalytic hydrogenation using, for example, a palladium catalyst (e.g. palladium/barium sulfate, palladium/activated carbon, palladium black, etc.), a rhodium catalyst or the like. This reaction is carried out in a solvent which does not interfere with the reaction. Examples of the solvent include amides (e.g. N,N-dimethylforamide, acetamide, etc.), alcohols (e.g. methanol, ethanol, etc.), cyclic ethers (e.g. tetrahydrofuran, etc.), organic carboxylic acids (e.g. acetic acid, propionic acid, etc.), water or appropriate mixtures thereof.

It is advantageous that the N-9-fluorenylmethyloxycarbonyl (Fmoc) group is eliminated by using an organic amine such as diethylamine, piperidine, morpholine, 4-dimethylaminopyridine or dicyclohexylamine. This reaction is carried out in a solvent which does not interfere with the reaction. Examples of the solvent include amides (e.g. N,N-dimethylformamide, acetamide, etc.), alcohols (e.g. methanol, ethanol, etc.) and appropriate mixtures thereof.

It is advantageous that the N-2,2,2-trichloroethyloxycarbonyl group is eliminated by using a metal (e.g. zinc, etc.) along with an organic carboxylic acid (e.g. acetic acid, propionic acid, etc.). This reaction is carried out in a solvent which does not interfere with the reaction. Such solvents include the above-mentioned organic carboxylic acids, alcohols (e.g. methanol, ethanol, etc.), water and appropriate mixtures thereof.

The deprotection reaction (deacylation) of the acylated hydroxyl group is carried out in contact with an acid in a solvent which does not interfere with the reaction. Such solvents include halogenated hydrocarbons (e.g. dichloromethane, chloroform, 1,2-dichloroethane, etc.), alcohols (e.g. methanol, ethanol, etc.), water and appropriate mixtures thereof. Examples of the acid include haloacetic acids (e.g. trifluoroacetic acid, etc.), hydrohalogenic acids (e.g. hydrochloric acid, hydrobromic acid, etc.), among others.

It is advantageous that the O-benzyl (Bzl) group is eliminated by catalytic hydrogenation using, for example, a palladium catalyst (e.g. palladium/barium sulfate, palladium/activated carbon, palladium black) or a rhodium catalyst. In this case, a solvent known from the literature, such as a cyclic ether (e.g. tetrahydrofuran, etc.), is used singly or, depending on cases, as a mixture of another inert solvent [e.g. lower aliphatic acid amide (e.g. N,N-dimethylformamide, etc.)].

For the O-tetrahydropyranyl group or O-tert-butyl group, deprotection can be carried out by acid hydrolysis as in the case of the above-described deacylation.

The carboxyl protecting group can be eliminated by acid hydrolysis in the same manner as above. And, the benzyl ester, for example, can be eliminated by catalytic hydrogenation in the same manner as in the case of the elimination of O-benzyl group mentioned above. Further, methyl ester and ethyl ester, for example, can be eliminated by bringing them into contact with a base under the conditions which does not interfere with the reaction. As the solvent, use is made of alcohols (e.g. methanol, ethanol, etc.), cyclic ethers (e.g. tetrahydrofuran), water and appropriate mixtures thereof. The base is exemplified by sodium hydroxide, potassium hydroxide, sodium carbonate, potassium carbonate, etc.

The 2-(trimethylsilyl)ethyl group can be eliminated by allowing, for example, a salt of hydrofluoric acid, such as, especially, a salt of hydrofluoric acid with a quaternary nitrogen base (e.g. tetraethylammonium fluoride, etc.) in an adequate solvent under neutral conditions.

Compound (I) or a salt thereof thus produced is collected by a process of isolating peptide, for example, extraction, distribution, reprecipitation, crystallization, recrystallization, various kinds of chromatography, high performance liquid chromatography, or the like, after completion of the reaction.

The above-mentioned compound (II) or a salt thereof can be produced by subjecting a compound (IV) or a salt thereof to condensation with a compound represented by the general formula:

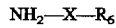

$$NH_2\text{—}X\text{—}R_6 \qquad (VI)$$

wherein X is of the same meaning as defined above, and $R_6$ stands for a protected carboxyl group, or a salt thereof, by a conventional means of peptide synthesis like that described above, followed by a deprotection reaction to eliminate the carboxyl protecting group.

Examples of the carboxyl-protecting group in the above-mentioned protected carboxyl group represented by $R_6$ include (1) $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.) optionally having 1 to 3 substituents selected from (a) nitro group, (b) halogen (e.g. bromine, chlorine, fluorine, etc.) and (c) alkanoyloxy groups (e.g. acetyloxy, propionyloxy, isopropionyloxy, butyryloxy, isobutyryloxy, valeryloxy, isovaleryloxy, pivaloyloxy, hexanoyloxy, etc.), (2) $C_{6-14}$ aryl groups (e.g. phenyl, naphthyl, etc.) optionally having 1 to 3 substituents selected from (a) nitro group, (b) halogen (e.g. bromine, chlorine, fluorine, etc.) and (c) $C_{1-4}$ alkoxy groups (e.g. methoxy, ethoxy, propoxy, isopropoxy, butoxy, isobutoxy, sec-butoxy, tert-butoxy, etc.), (3) $C_{7-12}$ aralkyl groups (e.g. benzyl, phenethyl, etc.) optionally having 1 to 3 substituents selected from (a) nitro group, (b) halogen (e.g. bromine, chlorine, fluorine, etc.) and (c) $C_{1-4}$ alkoxy groups (e.g. methoxy, ethoxy, propoxy, isopropoxy, butoxy, isobutoxy, sec-butoxy, tert-butoxy, etc.), (4) trityl group optionally having 1 to 3 substituents selected from (a) nitro group, (b) halogen (e.g. bromine, chlorine, fluorine, etc.) and (c) $C_{1-6}$ alkanoyl groups (e.g. formyl, acetyl, propionyl, isopropionyl, butyryl, etc.) and (5) tri- $C_{1-4}$ alkylsilyl groups (e.g. trimethylsilyl, triethylsilyl, etc.).

The above-mentioned compound (V) or a salt thereof can be produced by subjecting a compound represented by the general formula:

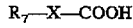

$$R_7\text{—}X\text{—}COOH \qquad (VII)$$

wherein X is of the same meaning as defined above and $R_7$ stands for a protected amino group, or a salt thereof to condensation with a compound (III) or a salt thereof by a conventional means of peptide synthesis like that described above.

Examples of the amino-protecting group in the protected amino group represented by $R_7$ above include (1) $C_{1-6}$ alkanoyl groups (e.g. formyl, acetyl, propionyl, isopropionyl, butyryl, isobutyryl, valery, isovaleryl, pivaloyl, hexanoyl, etc.) optionally having 1 to 3 substituents selected from (a) halogen atoms (e.g. chlorine, bromine, fluorine, etc.) and (b) nitro group, (2) $C_{7-11}$ arylcarbonyl groups (e.g. benzoyl, 1-naphthoyl, 2-naphthoyl, etc.) optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group, (3) $C_{8-13}$ aralkylcarbonyl groups (e.g. benzylcarbonyl, phenethylcarbonyl, etc.) optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group, (4) $C_{2-7}$ alkoxycarbonyl groups (e.g. methoxycarbonyl, ethoxycarbonyl, propoxycarbonyl, isopropoxycarbonyl, tert-butoxycarbonyl, etc.) optionally having 1 to 3 substituents selected from (a) halogen atoms (e.g. chlorine, bromine, fluorine, etc.) and (b) nitro group, (5) $C_{8-13}$ aralkyloxycarbonyl groups (e.g. benzyloxycarbonyl, phenylethyloxycarbonyl, etc.) optionally having substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group, (6) $C_{7-11}$ aryloxycarbonyl groups (e.g. phenoxycarbonyl, etc.) optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group, (7) $C_{6-10}$ arylsulfonyl groups (e.g. phenylsulfonyl, tosyl, etc.) optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group, (8) trityl group optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group) and (9) phthaloyl group optionally having 1 to 3 substituents selected from (a) halogen atoms (e.g. chlorine, bromine, fluorine, etc.), (b) $C_{1-4}$ alkyl groups (e.g. methyl, ethyl, propyl, isopropyl, butyl, isobutyl, sec-butyl, tert-butyl, etc.) and (c) nitro group.

The compound (I) of the present invention can also be produced as an alkali metal salt such as sodium salt or potassium salt, an alkaline earth metal salt such as calcium salt or magnesium salt, an acid-addition salt, especially a pharmaceutically acceptable acid-addition salt by a per se known method, as exemplified by salts formed with inorganic acids (e.g. hydrochloric acid, sulfuric acid and phosphoric acid) or with organic acids (e.g. acetic acid, propionic acid, citric acid, tartaric acid, malic acid, oxalic acid, methanesulfonic acid and octanesulfonic acid).

With respect to the salts of compounds (II) through (VII), the same applies as with salts of compound (I).

Structural formulae of the compounds produced by Working Examples described later are shown as follows.

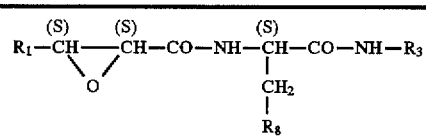

| Compound No. | $R_1$ | $R_3$ | $R_8$ |
|---|---|---|---|
| 1 | $COOC_2H_5$ | $(CH_2)_3OCH_3$ | Ph |
| 2 | COONa | $(CH_2)_3OCH_3$ | Ph |
| 3 | $COCC_2H_5$ | $(CH_2)_3OH$ | Ph |
| 4 | COONa | $(CH_2)_3OH$ | Ph |
| 5 | $COOC_2H_5$ | $(CH_2)_3OCOCH_3$ | Ph |
| 6 | COONa | $(CH_2)_3OCOCH_3$ | Ph |
| 7 | $COOC_2H_5$ | $(CH_2)_3SCH_3$ | Ph |
| 8 | COONa | $(CH_2)_3SCH_3$ | Ph |
| 9 | $COOC_2H_5$ | $(CH_2)_3OCH_3$ | $CH(CH_3)_2$ |
| 10 | COONa | $(CH_2)_3OCH_3$ | $CH(CH_3)_2$ |
| 11 | $COOC_2H_5$ | $(CH_2)_3OC_2H_5$ | Ph |
| 12 | COONa | $(CH_2)_3OC_2H_5$ | Ph |
| 13 | $COOC_2H_5$ | $(CH_2)_3O(i\text{-}Pr)$ | Ph |
| 14 | COONa | $(CH_2)_3O(i\text{-}Pr)$ | Ph |
| 15 | $COOC_2H_5$ | $(CH_2)_3OBu$ | Ph |
| 16 | COONa | $(CH_2)_3OBu$ | Ph |
| 17 | $COOC_2H_5$ | $(CH_2)_5OCH_3$ | Ph |
| 18 | COONa | $(CH_2)_5OCH_3$ | Ph |
| 19 | COOBzl | $(CH_2)_3OCH_3$ | Ph |
| 20 | COOPOM | $(CH_2)_3OCH_3$ | Ph |
| 21 | $CONHC_3H_7$ | $(CH_2)_3OCH_3$ | Ph |

(Ph stands for phenyl group, i-Pr stands for isopropyl group, Bu stands for butyl group, and POM stands for pivaloyloxymethyl group.)

The bioactivities of the compounds of this invention are described below. The compound (I) of this invention or salts thereof show a strong action of inhibiting thiol protease. Their inhibitory activities against cathepsin L and cathepsin B were determined by the methods described below. The results are shown in [Table 1] and [Table 2].

(a) Determination of cathepsin L inhibitory activity

To 75 µl of a reaction mixture containing 1 ng of human recombinant cathepsin L (those produced in Reference Examples 1 through 7 below were employed), 2 µM of dithiothreitol (hereinafter abbreviated as DTT), 1 mM of ethylenediaminetetraacetate disodium salt, 0.1M of a sodium acetate buffer solution (pH 5.5) and various concentrations of the sample, 25 µl of 20 µM benzyloxycarbonyl-L-phenylalanyl-L-arginine-4-methylcoumaryl-7-amide (hereinafter simply referred to as Z-Phe-Arg-7MCA, manufactured by Peptide Institute, Inc.) was added to initiate the reaction, and the reaction mixture was incubated at 37° C. for 20 minutes, followed by addition of 100 µl of a solution containing 100 mM of sodium monochloroacetate to suspend the reaction. The amount of liberated 4-methyl-7-aminocoumarin was determined at an excitation wavelength of 365 nm and a fluorescence wavelength of 450 nm, using a fluorophotometer (FCA: manufactured by Baxter Labs). The sample concentration required to cause 50% inhibition was expressed as the $IC_{50}$ value, with the fluorescence value obtained from the same reaction in the absence of the sample taken as 100%.

TABLE 1

| Compound No. | Inhibitory activity potency $IC_{50}$ (ng/ml) Cathepsin L |
|---|---|
| 2 | 3 |
| 6 | 5 |
| 8 | 3 |

(b) Determination of cathepsin B inhibitory activity

To 75 µl of a reaction mixture containing 30 ng of cathepsin B (produced by Sigma Chemical Co.), 2 µM DTT, 1 mM ethylenediaminetetraacetate disodium salt, 0.1M sodium acetate buffer (pH 5.5) and various concentrations of the sample, 25 µl of 20 µM Z-Phe-Arg-7MCA was added to initiate the reaction, and the reaction mixture was incubated at 37° C. for 20 minutes, followed by addition of 100 µl of a solution containing 100 mM sodium monochloroacetate to suspend the reaction. The amount of liberated 4-methyl-7-aminocoumarin was determined at an excitation wavelength of 365 nm and a fluorescence wavelength of 450 nm, using a fluorophotometer. The sample concentration required to cause 50% inhibition was expressed as the $IC_{50}$ value, with the fluorescence value obtained from the same reaction in the absence of the sample taken as 100%.

TABLE 2

| Compound No. | Inhibitory activity potency $IC_{50}$ (ng/ml) Cathepsin L |
|---|---|
| 8 | 2 |

Further, the compound (I) of this invention or salts thereof have an excellent activity of suppressing bone resorption. Their suppressive action against bone resorption as enhanced by PTH (parathyroid hormone) was determined by the method described below. The results are shown in [Table 3].

Determination of bone resorption suppressive activity

Femurs were aseptically isolated from female BALB/c mice at 8–10 weeks of age. After the bone marrow cavity was washed with a Ham's F-12 medium containing 10% (w/w) thermally inactivated fetal calf serum, 100 unit/ml penicillin G and 100 unit/ml streptomycin (hereinafter referred to as culture broth), each femur was added to 1 ml of the culture broth and precultured for 3 hours at 37° C. in the presence of 5% carbon dioxide gas and 95% air. Each bone was transferred to 1 ml of the culture broth supplemented with PTH (produced by Peptide Institute, Inc., final concentration of 1 µM) and the test compound (final concentration 10 µg/ml (and cultured for 7 more days, after which the total calcium content in the culture broth was determined using Calcium E-Test Wako (manufactured by Wako Pure Chemical Industries, Ltd.). The bone resorption suppressive activity of the test compound was calculated using the following equation:

Bone resorption suppressive activity(%)=100x(Cp–Cs)/(Cp–Cc)

Cc: Total calcium content in the culture broth containing neither PTH nor test compound
Cp: Total calcium content in the culture broth containing PTH
Cs: Total calcium content in the culture broth containing both PTH and test compound

TABLE 3

| Compound No. | Bone resorption suppressive activity (%) |
|---|---|
| 4 | 176 |
| 6 | 144 |
| 8 | 142 |

Toxicity study

Compound 1 caused no death in rats when it was orally administered at 300 mg/kg.

As described hereinbefore, the compound (I) or salts thereof have an inhibitory activity against substances having a thiol group as an active center such as thiol protease [e.g. cathepsins (e.g. cathepsin L, cathepsin B, cathepsin K), calpains (e.g. calpain I, calpain II), which can be used as thiol protease inhibitory agents useful for prophylactic and therapeutic agents of diseases caused by thiol protease (e.g. muscular dystrophy, aerocytic distal myopathy, myocardinal infarction, brain infarction, thrombosis, cataract, Alzheimer's disease, muscle atrophy, cancer metastasis, etc.). Besides, since substances inhibiting thiol protease shown an anti-inflammatory activity, the inhibitory agent of the present invention can be used as an anti-inflammatory agent as well.

Further, the compound (I) or salts thereof have bone resorption suppressive activity, which are used as prophylactic and therapeutic agents for bone diseases such as osteoporosis, hypercalcemia in malignancy, Paget's disease and chronic rheumatoid arthritis.

The compound (I) or salts thereof are low in toxicity, which can be safely used for mammals (e.g. dogs, cats, horses, monkeys, humans, etc.).

When compound (I) or a salt thereof is administered to, for example, a human, it can be safely administered orally or non-orally as such, or in the form of a pharmaceutical composition prepared by mixing with appropriate pharmaceutically acceptable carriers, excipients and diluents.

Examples of the above-mentioned pharmaceutical compositions include those for non-oral administration such as injections, and those for oral administration (e.g. powdery preparations, granular preparations, capsules and tablets).

These preparations can be produced by per se known methods in common use for pharmaceutical preparation.

For example, compound (I) or a salt thereof can be formulated into an aqueous injection along with a dispersing agent [e.g. Tween 80 (manufactured by Atlas Powder, USA), HCO 60 (manufactured by Nikko Chemicals), polyethylene glycol, carboxymethyl cellulose, sodium alginate, etc.), a preservative (e.g. methyl paraben, propyl paraben, benzyl alcohol, chlorobutanol, etc.), an isotonizing agent (e.g. sodium chloride, glycerol, sorbitol, glucose, etc.) and other additives.

Also, compound (I) or a salt thereof can be prepared into orally administrable preparations by compressive shaping in the presence, for example, of an excipient (e.g. lactose, sucrose, starch, etc.), a disintegrator (e.g. calcium carbonate, etc.), a binder (e.g. gum arabic, carboxymethyl cellulose, polyvinyl pyrrolidone, hydroxypropyl cellulose, etc.) or a lubricant (e.g. talc, magnesium stearate, polyethylene glycol 6000, etc.), followed by, depending on necessity, coating for taste-masking, enteric release or sustained release by a per se known method. Examples of the coating agent include ethyl cellulose, hydroxymethyl cellulose, polyoxyethylene glycol, cellulose acetate phthalate, hydroxypropylmethyl cellulose phthalate and Eudragit (manufactured by Rohm, Germany, methacrylic acid-acrylic acid copolymer).

The dose of compound (I) or a salt thereof when administered to humans ranges normally from about 1 mg to 2 g, preferably from about 10 mg to 2 g, more preferably from about 20 mg to 1 g daily in oral administration to an adult patient weighing 50 kg, varying with diseases, administration routes, ages of patients and severity of diseases.

The present invention is hereinafter described in more detail by means of, but not limited to, the following reference examples, working examples and formulation examples. Percent (%) ratios are percent by weight/volume, unless otherwise stated.

NMR spectra were taken using the Bruker AC-300 spectrometer. As the internal standard, 3-(trimethylsilyl) propionic acid-$d_4$ sodium salt was used in heavy water, and tetramethylsilane was used in other solvents; all δ values are expressed in ppm. The symbols used in the present specification have the following meanings: s; singlet, d; doublet, t; triplet, q; quartet, q; quintet, dd; double doublet, dt; double triplet, ddd; double double doublet, m; multiplet, br; broad.

Reference Example 1
(Cloning of cathepsin L cDNA of human renal origin)

To amplify human cathepsin cDNA by the polymerase chain reaction (PCR) method, the following four primers were synthesized taking a reported base sequence of cathepsin L of human renal origin [S. Gal and M. M. Gottesman, Biochemical Journal, Vol. 253, p. 303 (1988)] into consideration.

Sense primer No.1:
  5'-TTTTCAGGGGGCAGTAAGAT-3'
Sense primer No.2:
  5'-pCCGGATCCGGCTTTTTAGGATTGGTCTA-3'
Antisense primer No.3:
  5'-GGGGGCTGGTAGACTGAAGA-3'
Antisense primer No.4:
  5'-pCCGGATCCATTCCTCCCATGCATGCGCC-3'

Three μl of a solution of the human renal cDNA library λ gt11 (CLONTECH Laboratories, Inc.) and 50 μl of distilled water were mixed. After incubation at 95° C. for 5 minutes, the mixture was cooled rapidly in ice, to which were added two primers (Nos. 1 and 3 mentioned above; 50 pmol each). The reaction was carried out as directed in the instruction manual for the kit supplied by Cetus/Perkin-Elmer, in which a series of reactions at 94° C. for 1 minute, 55° C. for 2 minutes and 72° C. for 3 minutes was repeated in 50 cycles. To the reaction mixture, two other primers (Nos. 2 and 4 above; 50 pmol each) were added, substantially the same reaction as above was carried out. The PCR product was separated by electrophoresis on 1.2% agarose gel; an amplified DNA fragment was detected at a position corresponding to the size (1132 bp) expected from the base sequence of cathepsin L of human renal origin. This DNA fragment was recovered from the gel and subcloned to the plasmid vector pBluescript®IISK+ (manufactured by STRATAGENE, Inc.). The base sequence of the cDNA portion was determined by the dideoxynucleotide synthetic chain termination method [J. Messing, et al., Nucleic Acid Research, 9, 309, (1981)]; it proved identical with the reported sequence. The plasmid containing this cDNA fragment was named pHCL-5.

Reference Example 2
[Expression of human cathepsin L in *Escherichia coli* MM294(DE3)]

The cDNA of Reference Example 1 was cleaved with restriction enzyme EcoRI and a 798 bp fragment (which encodes a part of the human cathepsin L precursor and the whole matured human cathepsin L) was recovered. To both ends of this fragment was ligated a BamHI linker (5'-pCCCGGATCCGGG-3'), and the ligation product was inserted to the plasmid vector pET-3c for expression in *Escherichia coli* [Methods in Enzymology, ed. D. V. Goeddel, Vol. 185, p. 68, Academic Press (1990)]. The thus-constructed plasmid was designated as pET-HClα. *Escherichia coli* MM294(DE3) was transformed with pET-HClα to express human cathepsin L in the presence of the T7 promoter [Methods in Enzymology, Vol. 185, p. 60 (1990)]. The thus-obtained *Escherichia coli* transformant [*Escherichia coli* JM109/pTBN-HCLneo, harboring the plasmid pTBN-HCLneo, has been deposited under accession number IFO 15341 at the Institute for Fermentation, Osaka (IFO) since Jun. 12, 1992, and under accession number FERM BP 3897 at the National Institute of Bioscience and Human-Technology (NIBH), Agency of Industrial Science and Technology, Ministry of International Trade and Industry, since Jun. 22, 1992] was cultured, and cells thus obtained were disrupted by ultrasonication and subjected to SDS-PAGE; a unique band appeared near 30 kDal, corresponding to human cathepsin L. Since the expressed product formed an inclusion body, human cathepsin L was roughly purified from the precipitated fraction of the ultrasonically disrupted transformant.

Reference Example 3

(Preparation of antiserum to recombinant human cathepsin L)

The roughly purified recombinant human cathepsin L described in Reference Example 2 was mixed with an equal amount of complete Freund's adjuvant, and about 1 ml of the mixture was inoculated to a rabbit. Later, a mixture of a roughly purified human cathepsin L and an equal amount of incomplete Freund's adjuvant was injected to the animal three times at 10-day interval, and blood was collected seven days after final injection. The blood thus collected was kept standing at 37° C. for 30 minutes and, then, at 4° C. overnight, followed by subjecting the resultant to centrifugation to prepare a human cathepsin L antiserum.

Reference Example 4

(Preparation of recombinant DNA for expression of human cathepsin L gene in animal cells)

After the plasmid pHCL-5, described in Reference Example 1, was digested with restriction enzyme BamHI, a fragment of human cathepsin L cDNA was recovered by agarose gel electrophoresis. Subsequently, this cDNA fragment was inserted to the restriction enzyme BglII site of the vector pTB551 for transient expression in animal cells [prepared by converting the EcoRI to BglII site in the plasmid pTB389 described by Ono et al. in Science, Vol. 236, p. 1116 (1989)] by the action of T4 DNA ligase and ATP, to yield the expression plasmid pTB-HCl. MuLV-LTR was inserted between the restriction enzyme HindIII and ClaI sites of pTB-HCl to yield the expression plasmid pTBN-HCL.

Reference Example 5

(Preparation of recombinant DNA for expression of human cathepsin L gene in animal cells)

To obtain an animal cell line that stably expresses human cathepsin L, the drug resistance marker neogene was inserted to the recombinant vector pTBN-HCL described in Reference Example 4 in the following manner: first, a fragment comprising the SV40 early promoter and the neogene was inserted between the restriction enzyme ClaI and SalI sites of plasmid pTBN-HCL to yield the plasmid pTBN-HCLneO.

Reference Example 6

(Expression of human cathepsin L gene in animal cells)

Using the plasmid described in Reference Example 5 (pTBN-HCLneo), mouse myeloma Sp2/0 cells were transformed as follows: Sp2/0 cells, cultivated in an ASF104 medium supplemented with 5% fetal calf serum FCS (5% FCS/ASF medium), were suspended in phosphate-buffered saline (PBS) (−)[the same as Dullbecco's PBS but $CaCl_2$ and $MgCl_2$ were removed] to adjust $1\times10^7$ cells/ml. Five hundred µl of this cell suspension was injected to a cuvette, 10 µg of said plasmid DNA was added, and the mixture was left standing on ice for 5 minutes. This liquid was pulsated at 125 µF and 300 V, using a gene pulser (manufactured by Bio-Rad Laboratories), and then again left standing on ice for 10 minutes. This liquid was transferred to 10 ml of a 5% FCS/ASF104 medium and cultured at 37° C. in the presence of 5% carbon dioxide. Forty-eight hours later, the culture was transferred to a selection medium (5% FCS/ASF104 medium containing 200 µg/ml G418) and cultured on a 24-well plate for two weeks. A number of colonies emerged, each of which was transferred to an ASF10 medium containing 200 µg/ml G418 and cultured, followed by Western blot analysis of the culture supernatant using the human cathepsin L antiserum prepared in Reference Example 3. In response to the antiserum, unique bands corresponding to molecular weights of about 40,000 to 30,000 and lower molecular weights appeared; they were identified as a precursor of human cathepsin L and a product processed therefrom, estimated from these molecular weights. The culture supernatant was assayed for cathepsin L activity, in accordance with the method of A. J. Barrett and H. Kirschke [Methods in Enzymology, Vol. 80, p. 535 (1981)]; human cathepsin L activity was detected.

These findings confirm that transformant mouse myeloma cells expressing cathepsin L were obtained, which were designated as the mouse myeloma Sp-HCL26.

Reference Example 7

(Purification of human cathepsin L)

The strain obtained in Reference Example 6, showing high expression of cathepsin L, (the mouse myeloma Sp-HCL26, transformed with the plasmid pTBN-HCLneo, has been deposited under accession number IFO 50371 at the Institute of Fermentation, Osaka (IFO) since Jun. 16, 1992, and under accession number FERM BP 3902 at the National Institute of Bioscience and Human-Technology (NIBH), Agency of Industrial Science and Technology, Ministry of International Trade and Industry, since Jun. 24, 1992) was cultured in 20 ml of an ASF104 medium supplemented with 10% FCS and 200 µg/ml G418, after which it was transferred to 50 ml of a serum-free selection medium (ASF104 medium supplemented with 200 µg/ml G418) and cultured for 5 days. After the culture supernatant was applied to a column of CM-Sephadex C-50 (25×4.4 cm), the column was washed with buffer A (20 mM Sodium acetate, 1 mM EDTA, pH 5.5), followed by elution on a sodium chloride (NaCl) density gradient from 0 to 1M, to elute human cathepsin L near an NaCl concentration of about 0.4M. This fraction was applied to the Mono S column ($HR_{5/5}$) of an FPLC system (manufactured by Pharmacia), followed by column washing and human cathepsin L elution in the same manner as above. The human cathepsin L fraction, eluted near an NaCl concentration of about 0.36M, was concentrated to yield a purified standard preparation.

Reference Example 8

(2S,3S)-ethyl hydrogen trans-epoxysuccinate (2S,3S)-trans-epoxysuccinic acid diethyl ester as described in Tetrahedron, Vol. 36, p. 87 (1980) (15.1 g) was dissolved in ethanol (500 ml), to which was added 1N aqueous solution of sodium hydroxide (80.3 ml) under ice-cooling, and the mixture was stirred for 2 hours. To the reaction mixture was added water (100 ml), which was concentrated. The concentrate was adjusted to pH 2.5, to which sodium chloride was added to saturation, followed by extraction with ethyl acetate (150 ml×6). The ethyl acetate layer was washed with a saturated aqueous saline solution (100 ml×4) and then dried over anhydrous sodium sulfate, followed by concentration to yield the title compound (11.6 g) as a colorless oily product (yield 90%).

$^1$H NMR δ ppm ($CDCl_3$) 1.33(3H,t,J=7.2 Hz), 3.71(1H,d, J=1.7 Hz), 3.72(1H,d,J=1.6 Hz), 4.27(1H,dd,J=7.1, 10.8 Hz), 4.31(1H,dd,J=7.2, 10.8 Hz)

Working Example 1

N-[N-[(2S,3S)-3-trans-ethoxycarbonyloxysirane-2-carbonyl]-L-phenylalanyl]-1-amino-3-methoxypropane (2S,3S)-Ethyl hydrogen trans-epoxysuccinate produced in Reference Example 8 (5.00 g) was dissolved in dichloromethane (300 ml), and the solution was ice-cooled. To the solution were added L-phenylalanine benzylester p-toluenesulfonate (12.0 g, manufactured by Peptide Institute), HOBT (4.22 g), WSC (5.99 g) and triethylamine (3.74 ml). The mixture was stirred for 14 hours at room temperature. The reaction mixture was concentrated, which was dissolved in ethyl acetate. The solution was washed with a 10% aqueous solution of citric acid, water, a saturated aqueous solution of sodium hydrogen carbonate, a 2% aqueous solution of sodium hydrogen carbonate, water and a saturated aqueous saline solution, respectively, which was dried over anhydrous sodium sulfate, followed by concentration. The concentrate was subjected to a silica gel column chromatography (one liter), followed by elution with eluents prepared by adding ethyl acetate in sequence to hexane. From the fraction eluted with 30%(v/v) ethyl acetate, N-[(2S,3S)-3-trans-ethoxycarbonyloxysirane-2-carbonyl]-L-phenylalanine benzylester (8.56 g) was obtained as a white powdery product (yield 77%).

$[\alpha]_D$+55° (c 0.51, $CHCl_3$, 26° C.)

Elemental Analysis for $C_{22}H_{23}NO_6$:

Calcd.: C; 66.49, H; 5.83, N; 3.52 (%)

Found: C; 66.38, H; 5.82, N; 3.33 (%)

$^1H$ NMR δ ppm ($CDCl_3$) 1.29(3H,t,J=7.1 Hz), 3.03(1H,dd, J=6.6, 13.9 Hz), 3.16(1H,d,J=1.9 Hz), 3.20(1H,dd,J=5.9, 13.9 Hz), 3.62(1H,d,J=1.9 Hz), 4.23(2H,m), 4.87(1H,ddd, J=6.2, 6.3, 8.0 Hz), 5.18(2H,dd,J=12.1, 20.1 Hz), 6.54 (1H,d,J=8.0 Hz), 6.97(2H,m), 7.21–7.41(8H,m)

A portion of the compound thus produced (1.50 g) was dissolved in methanol (50 ml), to which was added 10% palladium/activated carbon [10% (w/w), manufactured by Japan Engelhard Corp., 150 mg]. The mixture was stirred for 1.5 hour at room temperature under hydrogen atmosphere. The catalyst was filtered off, then the filtrate was concentrated to give N-[(2S,3S)-3-trans-ethoxycarbonyloxysirane-2-carbonyl]-L-phenylalanine (1.11 g) as a white powdery product (yield 96%).

The compound thus obtained (1.00 g) was dissolved in N,N-dimethylformamide (33 ml), to which were added, under ice-cooling, 3-methoxypropylamine (365 μl, manufactured by Wako Pure Chemical Industries, Ltd.), HOBT (484 mg) and WSC (686 mg). The mixture was stirred for 16 hours at room temperature. The reaction mixture was concentrated, to which was added ethyl acetate. The mixture was washed successively with, a 10% aqueous solution of citric acid, water, a saturated aqueous solution of sodium hydrogen carbonate, a 2% aqueous solution of sodium hydrogen carbonate, water and a saturated aqueous saline solution, and then dried over anhydrous sodium sulfate, which was subjected to a silica gel column chromatography (100 ml). Elution was carried out with chloroform eluents sequentially supplemented with methanol. From the fraction eluted with 1% (v/v) methanol, the titled compound (compound 1; 800 mg) was obtained as a white powdery product (yield 65%).

$[\alpha]_D$+34° (c 0.60, $CHCl_3$, 25° C.)

Elemental Analysis for $C_{19}H_{26}N_2O_6$:

Calcd.: C; 60.30, H; 6.93, N; 7.40 (%)

Found: C; 60.09, H; 6.88, N; 7.50 (%)

$^1H$ NMR δ ppm ($CDCl_3$) 1.30(3H,t,J=7.1 Hz), 1.66(2H,m), 3.00(1H,dd,J=7.2, 13.7 Hz), 3.08(1H,dd,J=7.5, 13.7 Hz), 3.13(1H,d,J=1.9 Hz), 3.26(3H,s), 3.29(2H,m), 3.36(2H, m), 3.62(1H,d,J=1.9 Hz), 4.24(2H,m), 4.55(1H,dt,J=8.0, 7.4 Hz), 6.29(1H,t,J=4.9 Hz), 6.72(1H,d,J=8.1 Hz), 7.17 (2H,m), 7.30(3H,m)

Working Example 2

N-[N-[(2S,3S)-3-trans-carboxyoxirane-2-carbonyl]-L-phenylalanyl]-1-amino-3-methoxypropane monosodium salt Compound 1 (200 mg) was dissolved in methanol (10 ml), to which was added, under ice-cooling, a 1N aqueous solution of sodium hydroxide (581 μl, 1.1 equivalent). The mixture was stirred for one hour at room temperature. To the reaction mixture was added water, whose pH was adjusted to 7.0, followed by concentration. The concentrate was subjected to a Diaion HP-20 (20 ml, manufactured by Mitsubishi Chemical Industries, Ltd.) column chromatography. The column was washed with water, which was subjected to elution with a 50% (v/v) aqueous solution of methanol. The eluate was concentrated, which was lyophilized to give the titled compound (compound 2; 168 mg) as a white powdery product (yield 85%).

$[\alpha]_D$+46° (c 0.52, $H_2O$, 25° C.)

Elemental Analysis for $C_{17}H_{21}N_2O_6Na \cdot 0.5H_2O$:

Calcd.: C; 53.54, H; 5.81, N; 7.35, Na; 6.03 (%)

Found: C; 53.37, H; 5.86, N; 7.16, Na; 5.87 (%)

$^1H$ NMR δ ppm ($D_2O$) 1.61(2H,m), 3.03(1H,dd,J=8.0, 13.6 Hz), 3.09(1H,m), 3.14(1H,dd,J=7.5, 13.6 Hz), 3.19(1H, m), 3.22(1H,d,J=2.1 Hz), 3.28(2H,m), 3.30(3H,s), 3.50 (1H,d,J=2.1 Hz), 4.55(1H,t,J=7.9 Hz), 7.27(2H,m), 7.38 (3H,m)

Working Example 3

N-[N-[(2S,3S)-3-trans-ethoxycarbonyloxirane-2-carbonyl]-L-phenylalanyl]-3-amino-1-propanol In substantially the same manner as in Working Example 1, N-[(2S,3S)-3-trans-ethoxycarbonyloxirane-2-carbonyl]-L-phenylalanine (2.50 g) was condensed with 3-amino-1-propanol (685 μl, manufactured by Wako Pure Chemical Industries, Ltd.) to give the titled compound (compound 3; 1.86 g) as a white powdery product (yield 63%).

$[\alpha]_D$+23° (c 0.53, $CHCl_3$, 25° C.)

Elemental Analysis for $C_{18}H_{24}N_2O_6 \cdot 0.25HCl_3$:

Calcd.: C; 54.26, H; 6.04, N; 6.90 (%)

Found: C; 54.02, H; 6.02, N; 7.00 (%)

$^1H$ NMR δ ppm ($CDCl_3$) 1.30(3H,t,J=7.1 Hz), 1.61(2H,m), 2.67(1H,br s), 3.01(1H,dd,J=7.5, 13.7 Hz), 3.10(1H,dd, J=7.6, 13.8 Hz), 3.15(1H,d,J=1.9 Hz), 3.34(2H,m), 3.55 (2H,m), 3.63(1H,d,J=1.9 Hz), 4.24(2H,m), 4.59(1H,dt,J= 8.0, 7.6 Hz), 6.42(1H,t,J=5.6 Hz), 6.83(1H,d,J=8.2 Hz), 7.18(2H,m), 7.30(3H,m)

Working Example 4

N-[N-[(2S,3S)-3-trans-carboxyoxirane-2-carbonyl]-L-phenylalanyl]-3-amino-1-propanol monosodium salt The ethyl ester of compound 3 (500 mg) was subjected to alkali hydrolysis in substantially the same manner as in Working Example 2, followed by desalting with resin, concentration and lyophilization to give the titled compound (compound 4; 380 mg) as a white powdery product (yield 77%).

$[\alpha]_D$+47° (c 0.59, $H_2O$, 25° C.)

Elemental Analysis for $C_{16}H_{19}N_2O_6Na \cdot 0.5H_2O$:

Calcd.: C; 52.32, H; 5.49, N; 7.63, Na; 6.26 (%)

Found: C; 52.06, H; 5.61, N; 7.69, Na; 5.94 (%)

$^1H$ NMR δ ppm ($D_2O$) 1.60(2H,quintet,J=6.7 Hz), 3.03(1H, dd,J=8.1, 13.6 Hz), 3.13(1H,dd,J=7.6, 13.6 Hz), 3.15(1H, dd,J=6.7, 13.6 Hz), 3.22(1H,d,J=2.0 Hz), 3.23(1H,dd,J= 6.8, 13.7 Hz), 3.42(2H,t,J=6.6 Hz), 3.51(1H,d,J=2.1Hz), 4.56(1H,t,J=7.9 Hz), 7.27(2H,m), 7.38(3H,m)

Working Example 5
N-[N-[(2S,3S)-3-trans-ethoxycarbonyloxirane-2-carbonyl-L-phenylalanyl]-3-amino-1-acetoxypropane Compound 3 (500 mg) was dissolved in pyridine (12.5 ml), to which was added acetic anhydride (12.5 ml), and the mixture was left standing overnight at room temperature. The reaction mixture was concentrated, which was subjected to a silica gel (100 ml) column chromatography. Elution was carried out with a chloroform eluent supplemented with methanol sequentially added. The fraction eluted with 0.5% (v/v) methanol was concentrated, which was crystallized from ethyl acetate to give the titled compound (compound 5; 392 mg) as colorless needles (yield 70%).

$[\alpha]_D+26°$ (c 0.53, CHCl$_3$, 25° C.)

Elemental Analysis for C$_{20}$H$_{26}$N$_2$O$_7$:
  Calcd.: C; 59.10, H; 6.45, N; 6.89 (%)
  Found: C; 58.95, H; 6.43, N; 6.97 (%)

$^1$H NMR δ ppm (CDCl$_3$) 1.30(3H,t,J=7.2 Hz), 1.71(2H,m), 2.05(3H,s), 3.04(2H,m), 3.12(1H,d,J=1.8 Hz), 3.19(1H, m), 3.30(1H,m), 3.63(1H,d,J=1.8 Hz), 3.98(2H,t,J=6.1 Hz), 4.24(2H,m), 4.54(1H,m), 6.00(1H,t,J=5.8 Hz), 6.63 (1H,d,J=8.1 Hz), 7.17(2H,m), 7.30(3H,m)

Working Example 6
N-[N-[(2S,3S)-3-trans-carboxyoxirane-2-carbonyl]-L-phenylalanyl]-3-amino-acetoxypropane monosodium salt In substantially the same manner as in Working Example 5, compound 4 (200 mg) was acetylated, which was subjected to a preparative high performance liquid chromatography (column; YMC-Pack D-ODS-5, manufactured by YMC Co., Ltd; mobile phase; 15% (v/v)acetonitrile/0.02M phosphate buffer (pH6.3), flow rate; 10 ml/ml, detection; 214 nm). The fraction showing a single peak in analytical HPLC was collected and concentrated. The concentrate was subjected to a Diaion HP-20 (20 ml) column chromatography. The column was washed with water (40 ml), and then elution was carried out with water (40 ml), a 50% (v/v) aqueous solution of methanol (100 ml) and a 80% (v/v) aqueous solution of methanol (100 ml), successively. The eluate was concentrated and then lyophilized to give the titled compound (compound 6; 175 mg) as a white powdery product (yield 78%).

$[\alpha]_D+41°$ (c 0.59, H$_2$O, 25° C.)

Elemental Analysis for C$_{18}$H$_{21}$N$_2$O$_7$Na.0.5H$_2$O:
  Calcd.: C; 52.81, H; 5.42, N; 6.84, Na; 5.62 (%)
  Found: C; 53.02, H; 5.53, N; 6.82, Na; 5.09 (%)

1H NMR δ ppm (D$_2$O) 1.70(2H,quintet,J=6.3 Hz), 2.08(3H, s), 3.03(1H,dd,J=8.1, 13.6 Hz), 3.11(1H,dd,J=8.0, 13.9 Hz), 3.20(2H,m), 3.23(1H,d,J=2.0 Hz), 3.51(1H,d,J=2.0 Hz), 3.88(2H,t,J=6.3 Hz), 4.55(1H,t,J=7.9 Hz), 7.32(5H, m)

Working Example 7
N-[N-[(2S,3S)-3-trans-ethoxycarbonyloxirane-2-carbonyl]-L-phenylalanyl]-1-amino-3-methylthiopropane In substantially the same manner as in Working Example 1, N-[(2S,3S)-3-trans-ethoxycarbonyloxirane-2-carbonyl]-L-phenylalanine (1.00 g) was condensed with 3-methylthiopropylamine (357 μl, manufactured by Tokyo Kasei Kogyo, Co., Ltd.). The condensate was crystallized from ethyl acetate - hexane to give the titled compound (compound 7; 739 mg) as colorless needles (yield 58%).

$[\alpha]_D+27°$ (c 0.56, CHCl$_3$, 25° C.)

Elemental Analysis for C$_{19}$H$_{26}$N$_2$O$_5$S:
  Calcd.: C; 57.85, H; 6.64, N; 7.10, S; 8.13 (%)
  Found: C; 57.63, H; 6.52, N; 6.80, S; 8.24 (%)

$^1$H NMR δ ppm (CDCl$_3$) 1.31(3H,t,J=7.2 Hz), 1.69(2H,m), 2.06(3H,s), 2.38(2H,m), 3.04(2H,m), 3.14(1H,d,J=1.9 Hz), 3.29(2H,m), 3.63(1H,d,J=1.8 Hz), 4.25(2H,m), 4.54 (1H,q,J=7.7 Hz), 5.90(1H,t,J=5.4 Hz), 6.67(1H,d,J=8.0 Hz), 7.18(2H,m), 7.30(3H,m)

Working Example 8
N-[N-[(2S,3S)-3-trans-carboxyoxirane-2-carbonyl]-L-phenylalanyl]-1-amino-3-methylthiopropane monosodium salt In substantially the same manner as in Working Example 2, compound 7 (100 mg) was subjected to alkali hydrolysis of ethyl ester, which was desalted with resin, followed by concentration and lyophilization to yield the title compound (compound 8; 90.4 mg) as a white powdery product (yield 92%).

$[\alpha]_D+43°$ (c 0.55, H$_2$O, 25° C.)

Elemental Analysis for C$_{17}$H$_{21}$N$_2$O$_5$SNa.1.3H$_2$O:
  Calcd.: C; 49.58, H; 5.78, N; 6.80, S; 7.79, Na; 5.58 (%)
  Found: C; 49.58, H; 5.50, N; 6.50, S; 7.84, Na; 5.47 (%)

1H NMR δ ppm (D$_2$O) 1.61(2H,m), 2.04(3H,s), 2.25(2H,t, J=7.4 Hz), 3.07(3H,m), 3.24(1H,d,J=1.9 Hz), 3.25(1H, m), 3.50(1H,d,J=1.9 Hz), 4.54(1H,t,J=7.9 Hz), 7.32(5H, m)

Working Example 9
N-[N-[(2S,3S)-3-trans-ethoxycarbonyloxirane-2-carbonyl]-L-leucyl]-1-amino-3-methoxypropane In substantially the same manner as in Working Example 1, (2S,3S)-ethyl hydrogen trans-epoxysuccinate (0.77 g) was condensed with L-leucine benzylester p-toluenesulfonate (1.89 g, manufactured by Peptide Institute) to yield N-[(2S,3S)-3-trans-ethoxycarbonyloxirane-2-carbonyl]-L-leucine benzylester (1.62 g) as a colorless oily product (yield 93%).

The benzyl group of the compound thus obtained (1.60 g) was subjected to deprotection by means of catalytic reduction with palladium/activated charcoal to afford N-[(2S,3S)-3-trans-ethoxycarbonyloxirane-2-carbonyl]-L-leucine (1.02 g) as a colorless oily product (yield 96%).

The compound thus obtained (800 mg) was condensed with 3-methoxypropylamine (372 μl) to give the title compound (compound 9; 480 mg) as a white powdery product (yield 46%).

$[\alpha]_D+11°$ (c 0.62, CHCl$_3$, 25° C.)

Elemental Analysis for C$_{16}$H$_{28}$N$_2$O$_6$:
  Calcd.: C; 55.80, H; 8.19, N; 8.13 (%)
  Found: C; 55.62, H; 7.96, N; 8.46 (%)

$^1$H NMR δ ppm (CDCl$_3$) 0.92(3H,d,J=6.2 Hz), 0.94(3H,d, J=6.2 Hz), 1.32(3H,t,J=7.2 Hz), 1.52(2H,m), 1.66(1H,m), 1.78(2H,m), 3.35(3H,s), 3.38(2H,m), 3.47(1H,d,J=1.8 Hz), 3.48(2H,t,J=5.7 Hz), 3.69(1H,d,J=1.9 Hz), 4.27(2H, m), 4.38(1H,dt,J=5.9, 8.5 Hz), 6.56(1H,br s), 6.63(1H,d, J=8.3 Hz)

Working Example 10
N-[N-[(2S,3S)-3-trans-carboxyoxirane-2-carbonyl]-L-leucyl]-1-amino-3-methoxypropane monosodium salt In substantially the same manner as in Working Example 2, compound 9 (100 mg) was subjected to alkali hydrolysis of ethyl ester, which was desalted with resin, followed by concentration and lyophilization to afford the title compound (compound 10; 78 mg) as a white powdery product (yield 78%).

$[\alpha]_D+20°$ (c 0.51, H$_2$O, 26° C.)

Elemental Analysis for C$_{14}$H$_{23}$N$_2$O$_6$Na.0.4H$_2$O:
  Calcd.: C; 48.66, H; 6.94, N; 8.11, Na; 6.65 (%)
  Found : C; 48.56, H; 7.03, N; 8.42, Na; 6.70 (%)

$^1$H NMR δ ppm (D$_2$O) 0.88(3H,d,J=6.1 Hz), 0.92(3H,d,J= 6.1 Hz), 1.60(3H,m), 1.76(2H,quintet,J=6.5 Hz), 3.21(1H, dt,J=13.7, 6.7 Hz), 3.29(1H,dt,J=13.6, 6.7 Hz), 3.33(3H, s), 3.42(1H,d,J=2.1Hz), 3.46(2H,t,J=6.4 Hz), 3.56(1H,d, J=2.1 Hz), 4.30(1H,dd,J=9.5, 5.2 Hz)

Working Example 11
N-[N-[(2S,3S)-3-trans-ethoxycarbonyloxirane-2-carbonyl]-L-phenylalanyl]-1-amino-3-ethoxypropane In substantially the same manner as in Working Example 1, N-[(2S,3S)-3-trans-ethoxycarbonyloxirane-2-carbonyl]-L-phenylalanine (732 mg) was condensed with 3-ethoxypropylamine (314 µl, manufactured by Wako Pure Chemical Industries, Ltd.) to afford the title compound (compound 11; 461 mg) as a white powdery product (yield 49%).

$[\alpha]_D$+35° (c 0.59, $CHCl_3$, 26° C.)

Elemental Analysis for $C_{20}H_{28}N_2O_6 \cdot 0.2H_2O$:
  Calcd.: C; 60.65, H; 7.23, N; 7.07 (%)
  Found: C; 60.66, H; 7.12, N; 7.10 (%)

$^1$H NMR δ ppm ($CDCl_3$) 1.17(2H,t,J=7.0 Hz), 1.31(3H,t,J=7.0 Hz), 1.55–1.78(2H,m), 2.99(1H,dd,J=7.5, 13.5 Hz), 3.08(1H,dd,J=7.5, 13.5 Hz), 3.12(1H,d,J=2.0 Hz), 3.23–3.49(6H,m), 3.61(1H,d,J=2.0 Hz), 4.15–4.33(2H, m), 4.52(1H,dt,J=8.0, 7.5 Hz), 6.32(1H,br), 6.71(1H,d,J=8.0 Hz), 7.11–7.37(5H,m)

Working Example 12
N-[N-[(2S,3S)-3-trans-carboxyoxirane-2-carbonyl]-L-phenylalanyl]-1-amino-3-ethoxypropane monosodium salt In substantially the same manner as in Working Example 2, compound 11 (100 mg) was subjected to alkali hydrolysis of ethyl ester, which was desalted with resin, concentrated and lyophilized to afford the title compound (compound 12; 98 mg) as a white powdery product (yield, quantitative).

$[\alpha]_D$+43° (c 0.52, $H_2O$, 26° C.)

Elemental Analysis for $C_{18}H_{23}N_2O_6Na \cdot 1.5H_2O$:
  Calcd.: C; 52.30, H; 6.34, N; 6.78, Na; 5.56 (%)
  Found: C; 52.24, H; 6.17, N; 6.51, Na; 5.47 (%)

1H NMR δ ppm ($D_2O$) 1.17(3H,t,J=7.0 Hz), 1.54–1.70(2H, m), 2.98–3.39(6H,m), 3.23(1H,d,J=2.0 Hz), 3.44–3.57 (2H,m), 3.52(1H,d,J=2.0 Hz), 4.56(1H,t,J=8.0 Hz), 7.23–7.47(5H,m)

Working Example 13
N-[N-[(2S,3S)-3-trans-ethoxycarbonyloxirane-2-carbonyl]-L-phenylalanyl]-1-amino-3-isopropoxypropane In substantially the same manner as in Working Example 1, N-[(2S,3S)-3-trans-ethoxycarbonyloxirane-2-carbonyl]-L-phenylalanine (757 mg) was condensed with 3-isopropoxypropylamine (385 µl, Tokyo Kasei Kogyo Co., Ltd.) to afford the titled compound (compound 13; 519 mg) as a white powdery product (yield 52%).

$[\alpha]_D$+36° (c 0.54, $CHCl_3$, 26° C.)

Elemental Analysis for $C_{21}H_{30}N_2O_6$:
  Calcd.: C; 62.15, H; 7.44, N; 6.89 (%)
  Found: C; 62.09, H; 7.34, N; 6.69 (%)

$^1$H NMR δ ppm ($CDCl_3$) 1.11(3H,t,J=6.0 Hz), 1.13(3H,d, J=6.0 Hz), 1.30(3H,t,J=7.0 Hz), 1.54–1.77(2H,m), 2.98 (1H,dd,J=7.0, 14.0 Hz), 3.08(dd,J=7.0, 14.0 Hz), 3.12 (1H,d,J=2.0 Hz), 3.24–3.57(5H,m), 3.61(1H,d,J=2.0 Hz), 4.14–4.34(2H,m), 4.51(1H,ddd,J=7.0, 7.0, 8.0 Hz), 6.38 (1H,br), 6.72(1H,d,J=8.0 Hz), 7.10–7.38(5H,m)

Working Example 14
N-[N-[(2S,3S)-3-trans-carboxyoxirane-2-carbonyl]-L-phenylalanyl]-1-amino-3-isopropoxypropane monosodium salt In substantially the same manner as in Working Example 2, compound 13 (123 mg) was subjected to alkali hydrolysis of ethyl ester, which was desalted with resin, followed by concentration and lyophilization to afford the title compound (compound 14; 120 mg) as a white powdery product (yield 99%).

$[\alpha]_D$+45° (c 0.52, $H_2O$, 26° C.)

Elemental Analysis for $C_{19}H_{25}N_2O_6Na \cdot 1.8H_2O$:
  Calcd.: C; 52.72, H; 6.66, N; 6.47, Na; 5.31 (%)
  Found: C; 52.80, H; 6.42, N; 6.50, Na; 5.49 (%)

$^1$H NMR δ ppm ($D_2O$) 1.14(3H,d,J=6.5 Hz), 1.15(3H,d,J=6.5 Hz), 1.53–1.68(2H,m), 2.98–3.40(6H,m), 3.23(1H,d, J=2.0 Hz), 3.51(1H,d,J=2.0 Hz), 3.55–3.71(1H,m), 4.56 (1H,t,J=8.0 Hz), 7.23–7.47(5H,m)

Working Example 15
N-[N-[(2S,3S)-3-trans-ethoxycarbonyloxirane-2-carbonyl]-L-phenylalanyl]-1-amino-3-butoxypropane In substantially the same manner as in Working Example 1, N-[(2S,3S)-3-trans-ethoxycarbonyloxirane-2-carbonyl]-L-phenylalanine (570 mg) was condensed with 3-butoxypropylamine (313 µl, Wako Pure Chemical Industries, Ltd.) to give the title compound (compound 15; 580 mg) as a white powdery product (yield 75%).

$[\alpha]_D$+34° (c 0.55, $CHCl_3$, 26° C.)

Elemental Analysis for $C_{22}H_{32}N_2O_6$:
  Calcd.: C; 62.84, H; 7.67, N; 6.66 (%)
  Found: C; 62.65, H; 7.55, N; 6.73 (%)

$^1$H NMR δ ppm ($CDCl_3$) 0.93(3H,t,J=7.3 Hz), 1.30(3H,t,J=7.2 Hz), 1.35(2H,m), 1.52(2H,m), 1.66(2H,m), 2.98(1H, dd,J=7.1, 13.6 Hz), 3.07(1H,dd,J=7.6, 13.7 Hz), 3.12(1H, d,J=1.9 Hz), 3.36(6H,m), 3.62(1H,d,J=1.9 Hz), 4.24(2H, m), 4.51(1H,dt,J=7.7, 7.5 Hz), 6.26(1H,t,J=5.0 Hz), 6.68 (1H,d,J=8.1 Hz), 7.16(2H,m), 7.30(3H,m)

Working Example 16
N-[N-[(2S,3S)-3-trans-carboxyoxirane-2-carbonyl]-L-phenylalanyl]-1-amino-3-butoxypropane monosodium salt In substantially the same manner as in Working Example 2, compound 15 (100 mg) was subjected to alkali hydrolysis of ethyl ester, which was desalted with resin, followed by concentration and lyophilization to afford the title compound (compound 16; 75 mg) as a white powdery product (yield 76%).

$[\alpha]_D$+38° (c 0.55, $H_2O$, 26° C.)

Elemental Analysis for $C_{20}H_{27}N_2O_6Na \cdot H_2O$:
  Calcd.: C; 55.55, H; 6.76, N; 6.48, Na; 5.32 (%)
  Found: C; 55.35, H; 6.55, N; 6.68, Na; 5.35 (%)

1H NMR δ ppm ($D_2O$) 0.89(3H,t,J=7.3 Hz), 1.32(2H,m), 1.52(2H,m), 1.60(2H,m), 3.08(4H,m), 3.22(1H,d,J=1.8 Hz), 3.28(2H,m), 3.44(2H,t,J=6.7 Hz), 3.50(1H,d,J=1.8 Hz), 4.54(1H,t,J=7.9 Hz), 7.27(2H,m), 7.37(3H,m)

Working Example 17
N-[N-[(2S,3S)-3-trans-ethoxycarbonyloxirane-2-carbonyl]-L-phenylalanyl]-1-amino-5-methoxypentane 5-Amino-1-pentanol (5.44 ml. manufactured by Tokyo Kasei Kogyo Co., Ltd.) was dissolved in methanol (110 ml). To the solution was added, under ice-cooling, di-tert-butyl dicarbonate (11.5 ml, manufactured by Wako Pure Chemical Industries, Ltd.), and the mixture was stirred for 16 hours at room temperature. The reaction mixture was concentrated, which was subjected to a silica gel column chromatography (500 ml). Elution was conducted with a hexane eluent supplemented with ethyl acetate sequentially. The fraction eluted with 40% to 100% (v/v) ethyl acetate was concentrated to give N-Boc-5-amino-1-pentanol (9.71 g) as a colorless oily product (yield 96%). A portion (3.00 g) of this product was dissolved in anhydrous tetrahydrofuran (60 ml). To the solution were added 60% sodium hydride (990 mg) and methyl iodide (3.09 ml). The mixture was stirred for 67 hours at room temperature. The reaction mixture was added to a 10% aqueous solution of ammonium chloride. The mixture was subjected to extraction with ether (100 ml×2). The ether layer was washed with water and a saturated aqueous saline solution, which was then dried over anhydrous sodium sulfate and concentrated. The concentrate was subjected to a silica gel column chromatography (100 ml).

Elution was conducted with a hexane eluent sequentially supplemented with ethyl acetate. From the fraction eluted with 30% (v/v) ethyl acetate, N-Boc-5-methoxypentylamine (730 mg) was obtained as a colorless oily product (yield 23%). This product was dissolved in 4N HCl/ethyl acetate (7 ml, manufactured by Kokusan Kagaku Co., Ltd.). The solution was left standing for one hour at room temperature. The reaction mixture was concentrated, and resulting powdery precipitate was collected by filtration to obtain 5-methoxypentylamine hydrochloride (511 mg) as a white powdery product (yield 99%).

A portion (400 mg) of this product was, in substantially the same manner as in Working Example 1, subjected to condensation using N-[(2S,3S)-3-trans-ethoxycarbonyloxirane-2-carbonyl]-L-phenylalanine (720 mg), triethylamine (399 μl), HOBT (351 mg) and WSC (498 mg) to afford the title compound (compound 17; 449 mg) as a white powdery product (yield 47%).

$[\alpha]_D+28°$ (c 0.52, $CHCl_3$, 26° C.)

Elemental Analysis for $C_{21}H_{30}N_2O_6 \cdot 0.2H_2O$:
  Calcd.: C; 61.78, H; 7.46, N; 6.86 (%)
  Found: C; 61.75, H; 7.34, N; 6.87 (%)

$^1$H NMR δ ppm ($CDCl_3$) 1.27(2H,m), 1.31(3H,t,J=7.2 Hz), 1.40(2H,m), 1.53(2H,m), 3.03(2H,d,J=7.6 Hz), 3.13(1H, d,J=1.9 Hz), 3.17(2H,m), 3.32(3H,s), 3.34(2H,t,J=6.4 Hz), 3.62(1H,d,J=1.8 Hz), 4.25(2H,m), 4.52(1H,dt,J=7.9, 7.6 Hz), 5.67(1H,t,J=5.4 Hz), 6.69(1H,d,J=8.0 Hz), 7.18 (2H,m), 7.30(3H,m)

Working Example 18
N-[N-(2S,3S)-3-trans-carboxyoxirane-2-carbonyl]-L-phenylalanyl]-1-amino-5-methoxypentane monosodium salt In substantially the same manner as in Working Example 2, compound 17 (100 mg) was subjected to alkali hydrolysis of ethyl ester, which was desalted with resin, followed by concentration and lyophilization to afford the title compound (compound 18; 93 mg) as a white powdery product (yield 95%).

$[\alpha]_D+53°$ (c 0.54, $H_2O$, 26° C.)

Elemental Analysis for $C_{19}H_{25}N_2O_6Na \cdot 1.3H_2O$:
  Calcd.: C; 53.84, H; 6.56, N; 6.61, Na; 5.42 (%)
  Found: C; 53.97, H; 6.67, N; 6.60, Na; 5.57 (%)

$^1$H NMR δ ppm ($D_2O$) 1.12(2H,m), 1.34(2H,m), 1.50(2H, m), 3.04(2H,m), 3.10(1H,dd,J=8.1, 13.3 Hz), 3.16(1H,dd, J=6.8, 13.5 Hz), 3.22(1H,d,J=2.1 Hz), 3.33(3H,s), 3.43 (2H,t,J=6.7 Hz), 3.50(1H,d,J=2.1 Hz), 4.54(1H,t,J=7.8 Hz), 7.26(2H,m), 7.36(3H,m)

Working Example 19
N-[N-[(2S,3S)-3-trans-benzyloxycarbonyloxirane-2-carbonyl]-L-phenylalanyl]-1-amino-3-methoxypropane Compound 2 (150 mg) was dissolved in N,N-dimethylformamide (15 ml). To the solution was added benzyl bromide (96 μl, manufactured by Wako Pure Chemical Industries, Ltd.). The mixture was stirred for 16 hours at room temperature. The reaction mixture was concentrated, which was dissolved in ethyl acetate. The solution was washed with water and a saturated aqueous saline solution, which was then dried over anhydrous sodium sulfate, followed by concentration. The concentrate was pulverized from ethyl acetate - hexane to give the title compound (compound 19; 149 mg) as a white powdery product (yield 84%).

$[\alpha]_D+28°$ (c 0.53, $CHCl_3$, 26° C.)

Elemental Analysis for $C_{24}H_{28}N_2O_6 \cdot 0.15H_2O$:
  Calcd.: C; 65.04, H; 6.40, N; 6.32 (%)
  Found: C; 65.00, H; 6.35, N; 6.39 (%)

$^1$H NMR δ ppm ($CDCl_3$) 1.65(2H,m), 2.98(1H,dd,J=7.1, 13.7 Hz), 3.04(1H,dd,J=7.6, 13.7 Hz), 3.18(1H,d,J=1.9 Hz), 3.25(3H,s), 3.30(4H,m), 3.64(1H,d,J=1.9 Hz), 4.54 (1H,dt,J=8.0, 7.5 Hz), 5.16(1H,d,J=12.1 Hz), 5.23(1H,d, J=12.1 Hz), 6.29(1H,t,J=5.2 Hz), 6.74(1H,d,J=8.1 Hz), 7.15(2H,m), 7.24(3H,m), 7.37(5H,m)

Working Example 20
N-[N-[(2S,3S)-3-trans-pivaloyloxymethyloxycarbonyloxirane-2-carbonyl]-L-phenylalanyl]-1-amino-3-methoxypropane In substantially the same manner as in Working Example 19, compound 2 (150 mg) was allowed to react with pivalic acid chloromethyl ester (174 μl, manufactured by Tokyo Kasei Kogyo, Co., Ltd.) to give the title compound (compound 20; 120 mg) as a white powdery product (yield 66%).

$[\alpha]_D+19°$ (c 0.54, $CHCl_3$, 26° C.)

Elemental Analysis for $C_{23}H_{32}N_2O_8 \cdot 0.5H_2O$:
  Calcd.: C; 58.34, H; 7.02, N; 5.92 (%)
  Found: C; 58.32, H; 6.79, N; 6.05 (%)

$^1$H NMR δ ppm ($CDCl_3$) 1.23(9H,m), 1.66(2H,m), 2.99(1H, dd,J=6.9, 13.7 Hz), 3.07(1H,dd,J=7.9, 13.8 Hz), 3.17(1H, d,J=1.8 Hz), 3.26(3H,s), 3.32(4H,m), 3.64(1H,d,J=1.8 Hz), 4.53(1H,m), 5.81(2H,s), 6.21(1H,br s), 6.67(1H,d, J=8.0 Hz), 7.16(2H,m), 7.29(3H,m)

Working Example 21
N-[N-[(2S,3S)-3-trans-propylcarbamoyloxirane-2-carbonyl]-L-phenylalanyl]-1-amino-3-methoxypropane Compound 1 (200 mg) was dissolved in methanol (10 ml), to which was added, under ice-cooling, an aqueous solution of a 1N sodium hydroxide (581 μl, 1.1 equivalent). The mixture was stirred for 30 minutes at room temperature and for another 30 minutes after addition of water (1.0 ml) at room temperature. To the reaction mixture was added water, whose pH was adjusted to 7.0, followed by concentration. After adjustment to pH 2.5, the concentrate was extracted with ethyl acetate (20 ml×3). The ethyl acetate layer was washed with a saturated aqueous saline solution (20 ml ×2), which was dried and concentrated to give N-[N-[(2S,3S)-3-trans-carboxyoxirane-2-carbonyl]-L-phenylalanyl]-1-amino-3-methoxypropane (164 mg) as a colorless oily product (yield 89%). A portion (140 mg) of this product was, in substantially the same manner as in Working Example 1, condensed with propylamine (33 μl, manufactured by Wako Pure Chemical Industries, Ltd.) to give the titled compound (compound 21; 69 mg) as a white powdery product (yield 44%).

Elemental Analysis for $C_{20}H_{29}N_3O_5$:
  Calcd.: C; 61.36, H; 7.47, N; 10.73 (%)
  Found: C; 61.12, H; 7.50, N; 10.59 (%)

$^1$H NMR δ ppm ($CDCl_3$) 0.91(3H,t,J=7.4 Hz), 1.52(2H,m), 1.64(2H,m), 3.02(2H,d,J=7.2 Hz), 3.22(2H,m), 3.23(1H, d,J=2.0 Hz), 3.25(3H,s), 3.28(2H,m), 3.33(2H,m), 3.43 (1H,d,J=2.0 Hz), 4.53(1H,m), 6.05(1H,t,J=5.8 Hz), 6.19 (1H,m), 6.78(1H,d,J=7.9 Hz), 7.17(2H,m), 7.29(3H,m)

Formulation Example

All the following components, including compound 1 as produced in Working Example 1, were mixed together and filled in gelatin capsules to yield a capsular preparation containing 30 mg of compound 1 per capsule.

| Compound 1 | 30 mg |
| Lactose | 100 mg |
| Corn starch | 40 mg |
| Magnesium stearate | 10 mg |
| Total | 180 mg |

The compound (I) or a salt thereof is used as a prophylactic and therapeutic agent for bone diseases such as osteoporosis, hypercalcemia in malignancy, Paget's disease and chronic rheumatoid arthritis. And, the compound (I) or a salt thereof has an inhibitory activity against thiol protease, which can also be used as a prophylactic and therapeutic agent of diseases caused by thiol protease.

What is claimed is:

1. A compound of the formula:

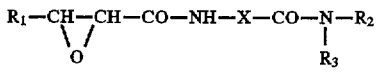

wherein $R_1$ represents an optionally esterified or amidated carboxyl group, X represents an optionally substituted divalent hydrocarbon residue, $R_2$ represents hydrogen or an optionally substituted hydrocarbon residue, $R_3$ represents an alkyl group which is substituted with a group selected from (1) hydroxyl, (2) $C_{1-6}$ alkoxy, (3) $C_{6-10}$ aryloxy (4) $C_{7-12}$ aralkyloxy, (5) $C_{1-6}$ alkanoyloxy or (6) $C_{7-11}$ arylcarbonyloxy, with the proviso that when the partial structural formula: —NH—X—CO— is leucine residue, $R_3$ is not a 3-hydroxy-3-methylbutyl group nor 4-hydroxy-3-methylbutyl group, or a salt thereof.

2. A compound of the formula:

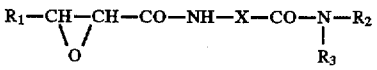

wherein $R_1$ represents an optionally esterified or amidated carboxyl group, X represents an optionally substituted divalent hydrocarbon residue, $R_2$ represents hydrogen or an optionally substituted hydrocarbon residue, $R_3$ represents an alkyl group which is substituted with a group bonded through $S(O)_n$, wherein n is 0, 1 or 2, or a salt thereof.

3. The compound according to claim 1, wherein $R_3$ is an alkyl group which is substituted with a $C_{1-6}$ alkoxy group.

4. The compound according to claim 2, wherein $R_3$ represents an alkyl group which is substituted with a group selected from (1) mercapto, (2) $C_{1-6}$ alkylthio, (3) $C_{6-10}$ arylthio, (4) sulfeno, (5) sulfino, (6) $C_{1-6}$ alkylsulfinyl, (7) $C_{6-10}$ arylsulfinyl, (8) sulfo, (9) $C_{1-6}$ alkylsulfonyl or (10) $C_{6-10}$ arylsulfonyl.

5. The compound according to claim 2, wherein the group bonded through $S(O)_n$ is $C_{1-14}$ hydrocarbon-$S(O)_n$ group.

6. The compound according to claim 5, wherein the $C_{1-14}$ hydrocarbon-$S(O)_n$ group is $C_{1-6}$ alkylthio group.

7. The compound according to claim 1 or 2, wherein $R_1$ is an optionally esterified carboxyl group.

8. The compound according to claim 1 or 2, wherein the partial structural formula: —NH—X—CO— is an α-amino acid residue.

9. The compound according to claim 8, wherein the α-amino acid residue is an aromatic amino acid residue.

10. The compound according to claim 8, wherein the α-amino acid residue is of L-configuration.

11. The compound according to claim 1 or 2, wherein X is a divalent hydrocarbon residue having a cyclic group.

12. The compound according to claim 1 or 2, wherein $R_2$ is hydrogen.

13. The compound according to claim 1 or 2, wherein $R_2$ is $C_{1-16}$ hydrocarbon residue.

14. The compound according to claim 1 or 2, wherein the alkyl group is $C_{1-15}$ alkyl group.

15. N-[N-[(2S,3S)-3-trans-ethoxycarbonyloxirane-2-carbonyl]-L-phenylalanyl]-1-amino-3-methoxypropane.

16. N-[N-[(2S,3S)-3-trans-ethoxycarbonyloxirane-2-carbonyl]-L-phenylalanyl]-1-amino-3-methylthiopropane.

17. A composition for inhibition of a thiol protease, which comprises a compound or a salt thereof as claimed in claim 1 or 2.

18. A pharmaceutical composition which comprises a compound or a salt thereof as claimed in claim 1 or 2.

19. A pharmaceutical composition for preventing or treating a bone disease, which comprises a compound or a salt thereof as claimed in claim 1 or 2.

20. The pharmaceutical composition according to claim 19, wherein the bone disease is osteoporosis.

21. A method for inhibiting a thiol protease in a mammal, which comprises administering an effective amount of the compound as claimed in claim 1 or 2 or a pharmaceutically acceptable salt thereof to the mammal.

22. A method for preventing or treating a bone disease in a mammal, which comprises administering an effective amount of the compound as claimed in claim 1 or 2 or a pharmaceutically acceptable salt thereof to the mammal.

23. The method according to claim 22, wherein the bone disease is osteoporosis.

* * * * *